(12) United States Patent
Kriesel et al.

(10) Patent No.: US 6,277,095 B1
(45) Date of Patent: Aug. 21, 2001

(54) FLUID DELIVERY DEVICE WITH FULL ADAPTER

(75) Inventors: Marshall S. Kriesel, St. Paul; Thomas N. Thompson, Richfield, both of MN (US)

(73) Assignee: Science Incorporated, Bloomington, MN (US)

( * ) Notice: Subject to any disclaimer, the term of this patent is extended or adjusted under 35 U.S.C. 154(b) by 0 days.

(21) Appl. No.: 09/312,590

(22) Filed: May 14, 1999

Related U.S. Application Data

(63) Continuation-in-part of application No. 09/250,030, filed on Feb. 12, 1999, which is a continuation-in-part of application No. 08/991,123, filed on Dec. 16, 1997, now Pat. No. 5,957,891, which is a continuation-in-part of application No. 08/606,090, filed on Feb. 23, 1996, now Pat. No. 5,779,676, which is a continuation-in-part of application No. 08/541,184, filed on Oct. 11, 1995, now Pat. No. 5,776,103.

(51) Int. Cl.[7] .................................................. A61M 37/00
(52) U.S. Cl. ..................... 604/132; 604/890.1; 604/246; 604/201; 128/DIG. 12
(58) Field of Search ..................... 604/132, 153, 604/246, 890.1, 131, 151, 118, 187, 201, 244, 200, 411, 412–415, 905, 93.01; 128/DIG. 12

(56) References Cited

U.S. PATENT DOCUMENTS

| | | |
|---|---|---|
| Re. 29,656 | 6/1978 | Chittendon et al. . |
| 4,411,662 | 10/1983 | Pearson . |
| 4,564,054 | 1/1986 | Gustavsson . |
| 4,927,423 | 5/1990 | Malmborg . |
| 4,936,841 | 6/1990 | Aoki et al. . |
| 5,117,875 | 6/1992 | Marrucchi . |
| 5,226,900 | 7/1993 | Bancsi et al. . |
| 5,267,957 | * 12/1993 | Kriesel et al. ........................ 604/85 |
| 5,354,278 | * 10/1994 | Kriesel ................................ 604/132 |
| 5,397,303 | 3/1995 | Sancoff et al. . |
| 5,419,771 | * 5/1995 | Kriesel ................................ 604/132 |
| 5,445,631 | 8/1995 | Uchida . |
| 5,531,683 | * 7/1996 | Kriesel et al. ........................ 604/89 |
| 5,533,993 | 7/1996 | Maier . |
| 5,653,686 | 8/1997 | Coulter et al. . |
| 5,700,244 | * 12/1997 | Kriesel ................................ 604/132 |
| 5,840,071 | * 11/1998 | Kriesel et al. ....................... 604/132 |
| 5,879,345 | 3/1999 | Aneas . |
| 5,891,129 | 4/1999 | Daubert et al. . |
| 5,962,794 | * 10/1999 | Kriesel et al. ..................... 73/861.47 |
| 5,993,421 | * 11/1999 | Kriesel ................................ 604/132 |
| 5,993,425 | * 11/1999 | Kriesel .................................. 604/91 |

* cited by examiner

*Primary Examiner*—Richard K. Seidel
*Assistant Examiner*—Chris Rodriguez
(74) *Attorney, Agent, or Firm*—James E. Brunton, Esq.

(57) ABSTRACT

A fluid delivery device for infusing medicinal fluids at a precisely controlled rate which includes adapter sleeve means for insuring that only a proper medicament can be used to fill the fluid reservoir of the apparatus. More particularly, the apparatus includes a unique polarity adapter that will mate only with a particular delivery device and positively prevent filling the reservoir of the device with a medicament that is incompatible with the delivery profile of the device. In one form of the invention, the polarity adapter includes a novel double-ended cannula that is carried within the polarity adapter and controls filling of the fluid reservoir.

30 Claims, 34 Drawing Sheets

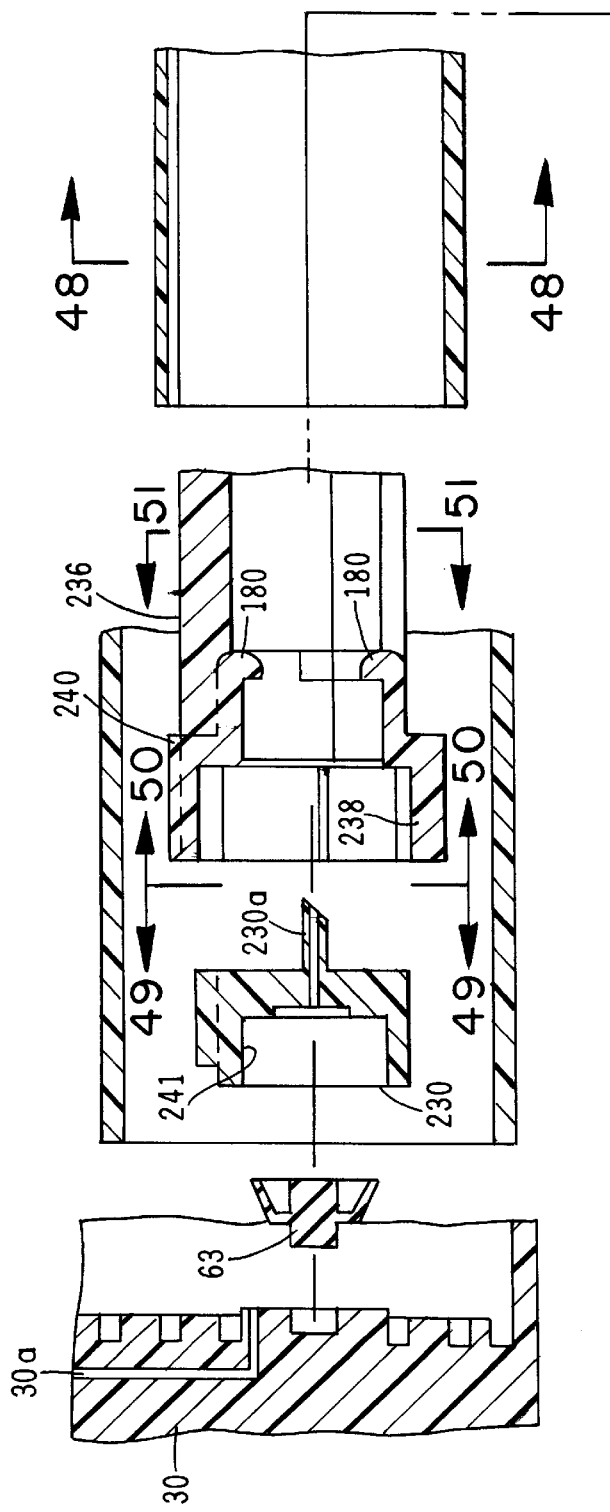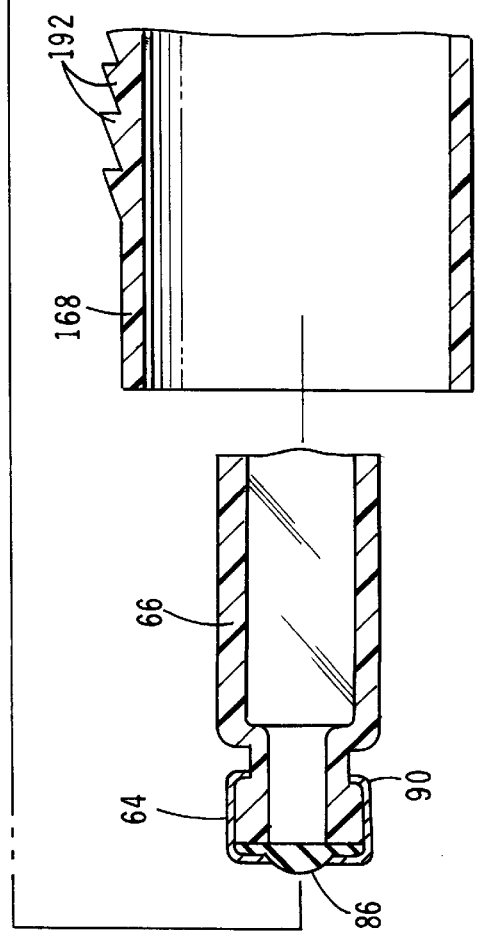
FIG. 47

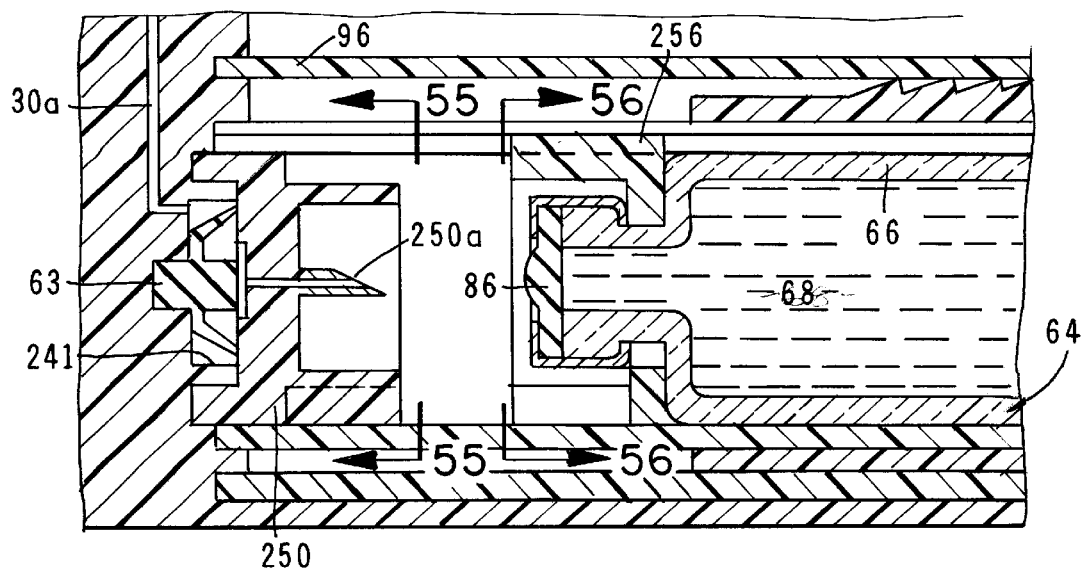
FIG.54
FIG.55
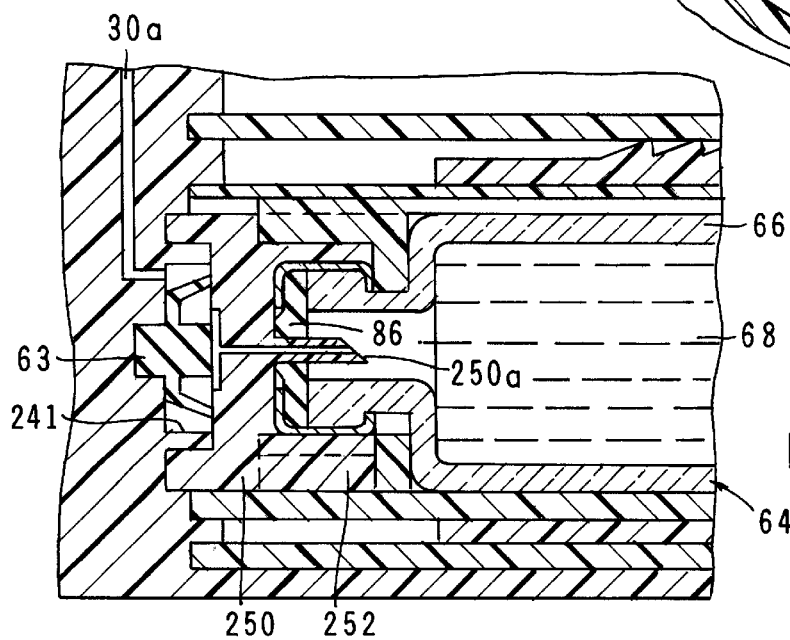
FIG.57

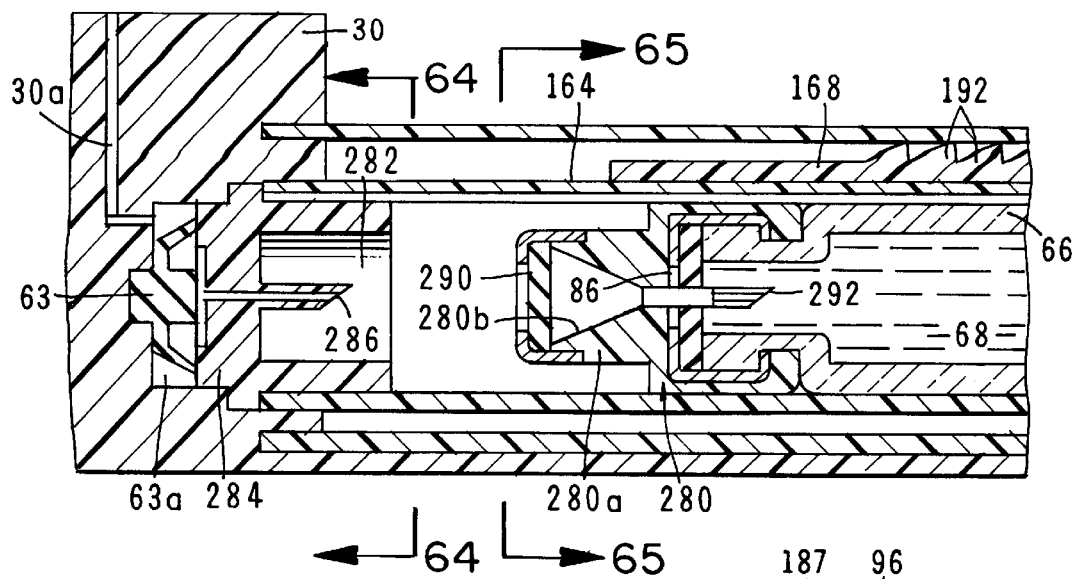
FIG.63
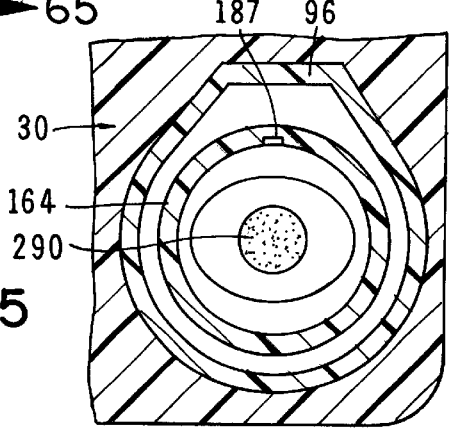
FIG.65
FIG.66
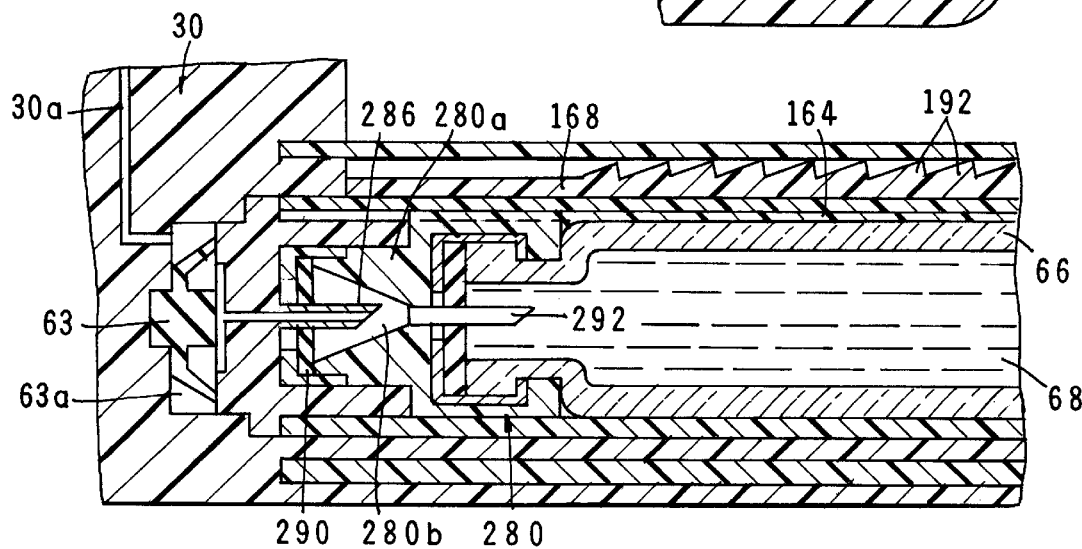

FLUID DELIVERY DEVICE WITH FULL ADAPTER

This is a Continuation-In-Part application of U.S. Ser. No. 09/250,030, filed Feb. 12, 1999; which is a Continuation-In-Part of application Ser. No. 08/991,123 filed Dec. 16, 1997 now U.S. Pat. No. 5,957,891 which is a Continuation-In-Part of application Ser. No. 08/606,090 filed Feb. 23, 1996 now U.S. Pat. No. 5,779,676 which is a Continuation-In-Part of application, U.S. Ser. No. 08/541,184, filed Oct. 11, 1995 now U.S. Pat. No. 5,776,103.

BACKGROUND OF THE INVENTION

1. Field of the Invention

The present invention relates generally to medicament dispensers. More particularly, the invention concerns a dispenser for use in controllably dispensing a liquid medicament from a reservoir disposed within the housing of the dispenser. The reservoir is typically filled using a medicament vial that is coupled with the dispenser housing by a novel polarity adapter.

2. Discussion of the Prior Art

A number of different types of medicament dispensers for dispensing medicaments to ambulatory patients have been suggested. Many of the devices seek either to improve or to replace the traditional gravity flow and hypodermic syringe methods which have been the standard for delivery of liquid medicaments for many years.

The prior art gravity flow methods typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

For those patients that require frequent injections of the same or different amounts of medicament, the use of the hypodermic syringe method of delivery is common. However for each injection, it is necessary to first draw the injection dose into the syringe, then check the dose and, after making certain that all air has been expelled from the syringe, finally, inject the dose. This cumbersome and tedious procedure creates an unacceptable probability of debilitating complications, particularly for the elderly and the infirm.

One example of the urgent need for an improved liquid delivery device for ambulatory patients can be found in the stringent therapeutic regimens used by insulin-dependent diabetics. The therapeutic objective for diabetics is to consistently maintain blood glucose levels within a normal range much as the normally functioning pancreas would do by secreting a very low level of extremely fast-acting insulin at a basal rate into the blood stream throughout the day and night. As will be appreciated from the discussion which follows, the apparatus of the present invention is uniquely suited to provide precise fluid delivery management at a low cost in those cases where a variety of precise dosage schemes are of utmost importance.

An additional aspect of the apparatus of the present invention is the provision of novel fill means for filling the reservoir of the device using a conventional medicament vial having a pierceable septum. An important feature of this fill means is a novel polarity adapter that is used to operably interconnect the medicament vial with the delivery device. In this regard, the polarity adapter is preferably fixedly connected to a standard medicament vial to provide a "keyed fitting" for the vial to insure that the fluid reservoir of the fluid dispenser can be filled only with the proper medicament. More particularly, with the polarity adapter connected to the drug vial, the novel design of the dispenser system is such that the user can connect the drug vial and polarity adapter only to a dispenser system having a delivery profile appropriate for the delivery to the patient of the particular drug contained within the medicament vial.

Because the embodiments of the invention described herein comprise improvements to the devices described in U.S. Ser. Nos. 08/991,123 filed Dec. 16, 1997, and Ser. No. 08/606,090 filed Feb. 23, 1997, application Ser. No. 08/991,123 is hereby incorporated by reference in its entirety as though fully set forth herein Similarly, application Ser. No. 08/606,090 is also hereby incorporated by reference in its entirety as though fully set forth herein.

Also helpful to a complete understanding of the present invention is an earlier filed application by the present inventor, which is identified by the Ser. No. 08/541,184. This application, which was filed on Oct. 11, 1995 is also incorporated by reference in its entirety as though fully set forth herein.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an tillage which comprises a part of the base assembly.

The present invention seeks to significantly improve over the prior art by providing a fluid delivery device having novel filling means for filling the fluid reservoir of the device only with a class of drug that is compatible with the delivery profile of the delivery device. This important safety feature is accomplished through the use of a unique polarity collar that is attached to the vial and is uniquely configured so that it will only mate with a fluid delivery device having the appropriate medicament delivery profile.

SUMMARY OF THE INVENTION

It is an object of the present invention to provide an apparatus of the character having a stored energy means for expelling fluids at a precisely controlled rate which includes safety means for insuring that only a proper medicament can be used to fill the fluid reservoir of the apparatus. More particularly, the apparatus includes a unique polarity adapter that will mate only with a particular delivery device and positively prevent filling the reservoir of the device with a medicament that is incompatible with the delivery profile of the device.

It is another object of the invention to provide an apparatus of the aforementioned character which is of simple construction, is highly reliable and is easily useable by lay persons in a non-hospital environment.

Another object of the invention is to provide an apparatus of the character described in the preceding paragraphs in which the polarity adapter can readily be connected to medicament vials of conventional construction.

Another object of the invention is to provide an apparatus as described in which the polarity adapter is appropriately keyed and configured so that it can be mated only with a particular fill adapter that, in turn, is keyed and configured so that it can only be mated with the housing of a particular fluid delivery device.

Another object of the invention is to provide an apparatus of the aforementioned character in which the polarity adapter has the cross-sectional shape of a truncated teardrop and in which the fill adapter also has the cross-sectional shape of a truncated tear drop.

Another object of the invention is to provide an apparatus of the character described which, due to its unique construction, can be manufactured inexpensively in large volume by automated machinery.

Other objects of the invention are set forth in the co-pending United States application which are incorporated herein by reference and still further objects will become apparent from the discussion which follows.

BRIEF DESCRIPTION OF THE DRAWINGS

FIG. 47 is an exploded, cross-sectional view of the assemblage shown in FIG. 44.

FIG. 54 is an enlarged, cross-sectional view of the receiving chamber and a portion of the dispenser housing of this latest embodiment illustrating the polarity adapter and vial assembly in position to be mated with the housing.

FIG. 55 is a cross-sectional view taken along lines 55—55 of FIG. 54.

FIG. 56 is a cross-sectional view taken along lines 56—56 of FIG. 54.

FIG. 57 is a cross-sectional view similar to FIG. 54 but showing the polarity adapter and vial assembly mated with the dispenser housing.

FIG. 63 is an enlarged, cross-sectional view of the forward portion of the delivery component showing the polarity adapter and medicament vial assembly mated and with the fluid delivery component.

FIG. 65 is a cross-sectional view taken a lines 65—65 of FIG. 63.

FIG. 66 is a cross-sectional view similar to FIG. 63, but showing the file assembly fully inserted into the delivery device housing

DESCRIPTION OF THE INVENTION

Figure 1:
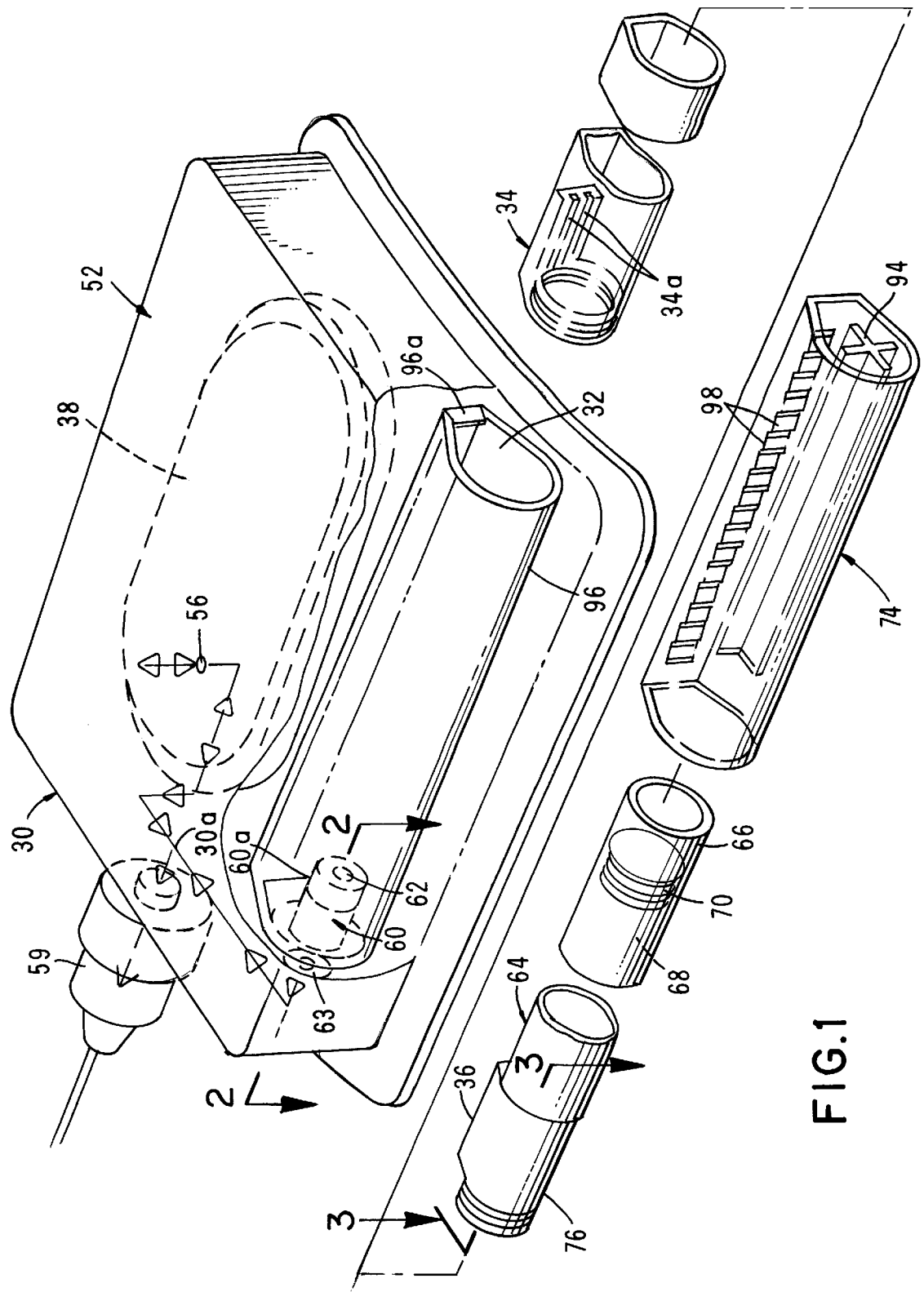
FIG. 1 is a generally perspective, exploded view of one form of the fluid delivery device of the present invention.

Referring to the drawings and particularly to FIGS. 1 through 7, one form of the fluid delivery device of the invention is there shown. This form of the invention comprises a housing assembly 30 having an elongated receiving chamber 32, a first adapter sleeve 34 that is telescopically receivable within chamber 32 and a novel polarity adapter 36 that is, in turn, telescopically receivable within adapter sleeve 34 in the manner shown in FIGS. 10 and 11.

Figure 24:
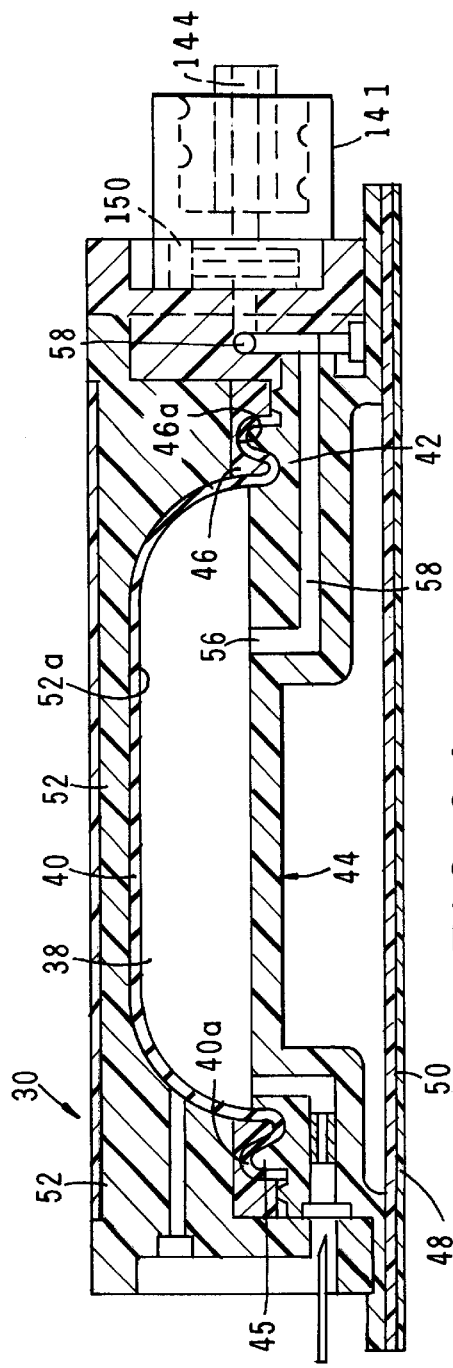
FIG. 24 is a cross-sectional view taken along lines 24—24 of FIG. 22.
Figure 25:
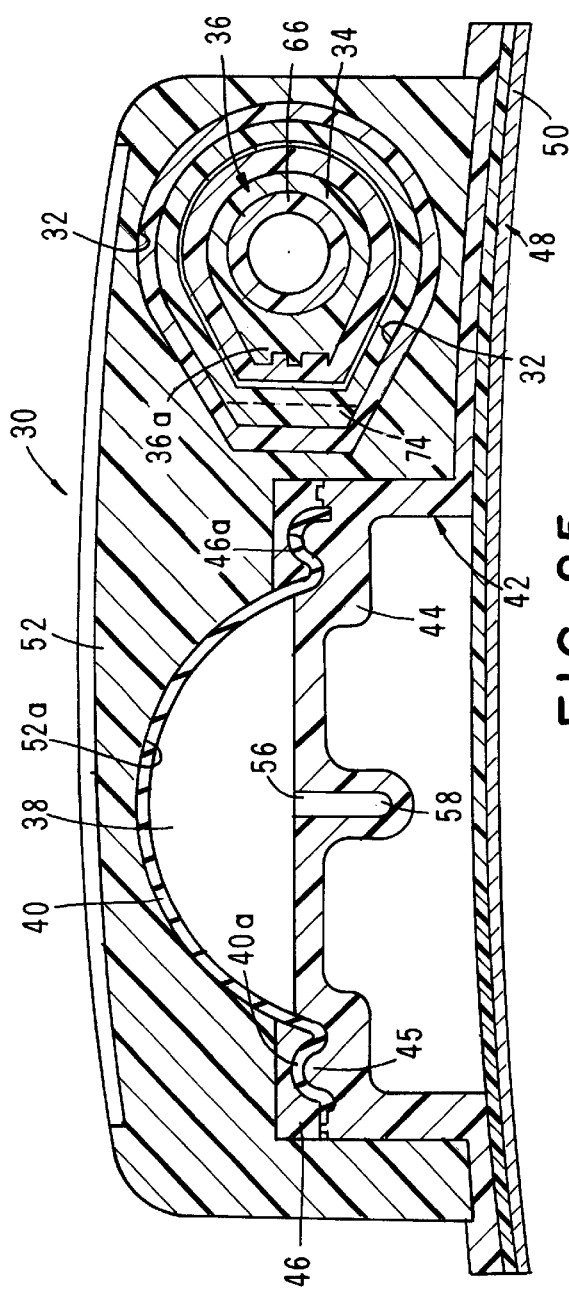
FIG. 25 is an enlarged, cross-sectional view taken along lines 25—25 of FIG. 22.

Provided within housing assembly 30 is a fluid reservoir 38 for containing the medicinal fluids to be delivered to the patient (FIGS. 24 and 25). As best seen by referring to FIGS. 24 and 25, this fluid reservoir is formed by a stored energy means, shown here as a distendable membrane 40, that is connected to a base assembly which forms a part of the housing assembly and is generally designated in the drawings by the numeral 42. Base assembly 42 includes a base component 44 having an upstanding tongue 45 and a clamping ring 46. Clamping ring 46 is provided with a groove 46a which receives tongue 45 and in the manner shown in FIGS. 24 and 25, functions to clamp the peripheral portion 40a of membrane 40 to base component 44. Base assembly 42 also includes a thin, planar shaped foam pad 48 which is affixed to the lower surface of base component 44. Pad 48 is provided with adhesive on both its upper and lower surfaces. The adhesive on the upper surface of the pad enables the pad to be securely affixed to the lower surface of base component 44 while the adhesive provided on the bottom surface of the pad permits the interconnection of the pad with a peel strip 50. When the device is to be used, the peel strip 50 can be stripped away from the pad so that the adhesive on the lower surface thereof will releasably affix the device to the patient's body. Housing 30 also includes a cover member 52 which is connected to base 44 by any suitable means such as adhesive bonding or sonic welding. Cover member 52 includes a concave portion which defines an inner elastomeric membrane engaging surface 52a (FIG. 24).

Figure 2:
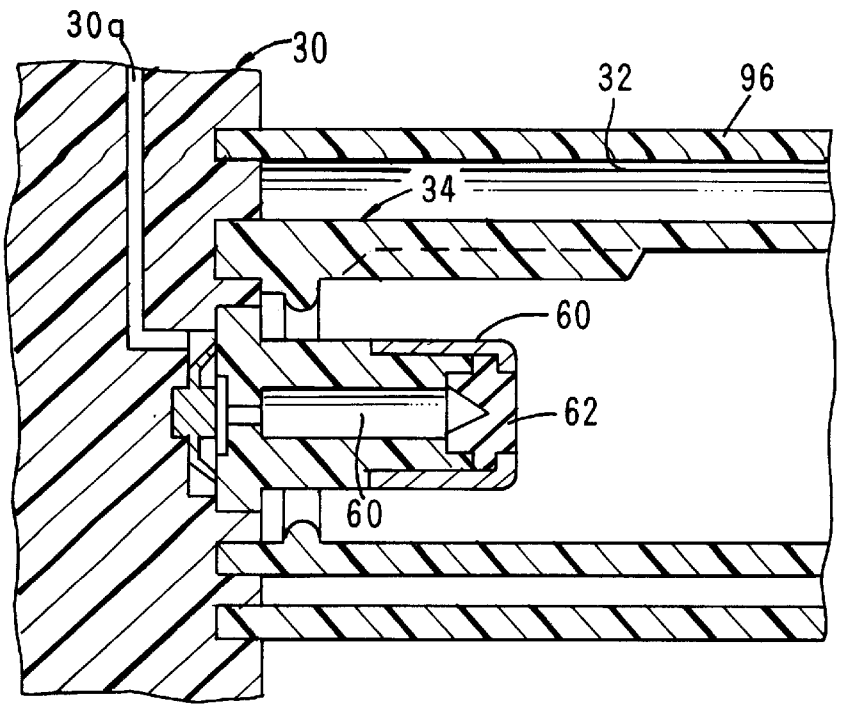
FIG. 2 is an enlarged, cross-sectional view taken along lines 2—2 FIG. 1.
Figure 22:
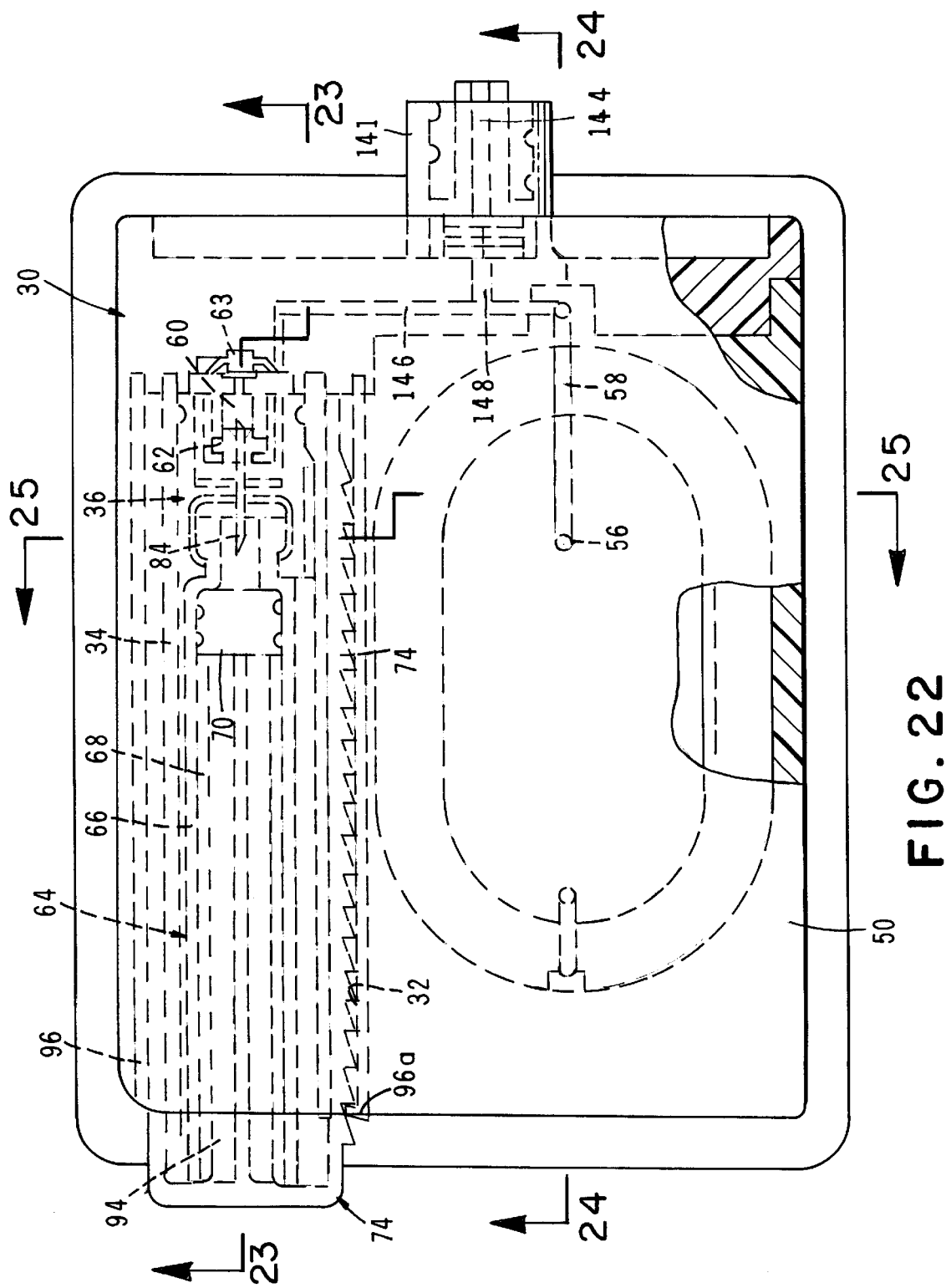
FIG. 22 is a top plan view of one form of the entire fluid delivery apparatus of the invention partly broken away to show internal construction.
Figure 23:
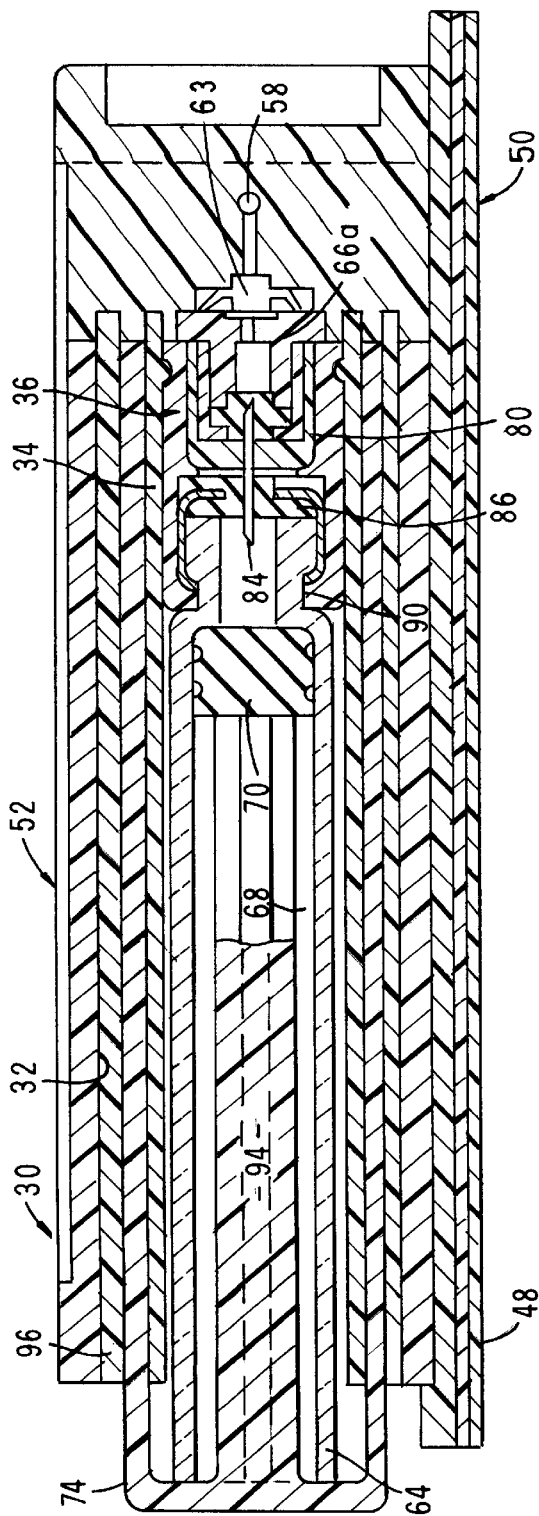
FIG. 23 is an enlarged, cross-sectional view taken along lines 23—23 of FIG. 22.

As best seen in FIGS. 22 and 24, reservoir 38 has an inlet/outlet port 56 which communicates with the infusion means of the invention via a passageway 58 formed in base component 44 (FIG. 24). The infusion means here comprises a conventional luer and delivery line assemblage generally designated by the numeral 59. Outlet 56 also communicates with fill chamber 60 which is closed by a first pierceable septum 62 (FIGS. 1 and 2). In the form of the invention shown in the drawings, fill chamber 60 is formed within a hub-like member 60a and is disposed within the previously identified receiving chamber 32 of housing assembly 30. Fill chamber 60 communicates with reservoir 38 via a conventional umbrella check valve 63 and an inlet passageway 30a (FIG. 2)

Figure 10:
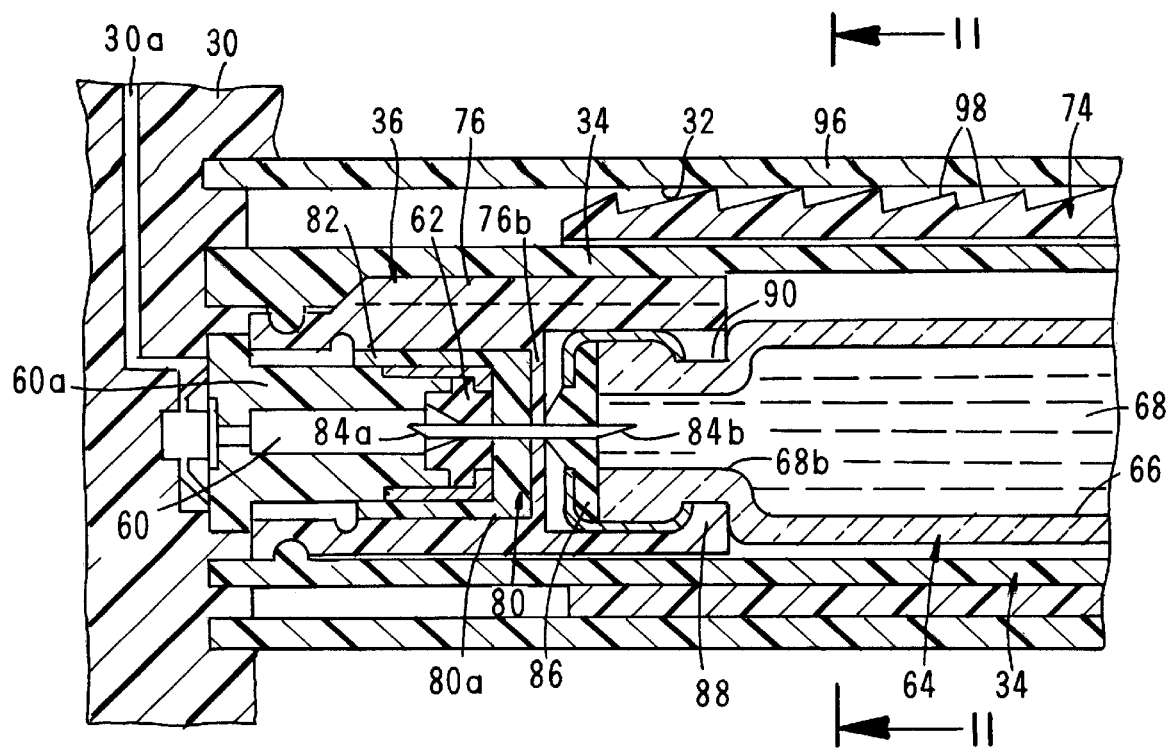
FIG. 10 is an enlarged, cross-sectional, fragmentary view of a portion of the fluid delivery device showing the medicament vial connected to the housing of the delivery device by means of the polarity adapter and showing the double-ended hollow cannula simultaneously piercing both the vial septum and the delivery device septum.

An important feature of the apparatus of the present invention is the fill means which is connected to housing assembly 30 and functions to fill the delivery device reservoir 38. This fill means here comprises a container assembly 64 which includes a conventional container, or vial 66 (FIGS. 1 and 10). Formed within the body portion of vial 66 is a fluid chamber 68 within which a plunger 70 is movable from a first location to a second spaced-apart location. Vial assembly 66 is telescopically receivable within a second sleeve assembly 74, the purpose of which will presently be described.

Figure 3:
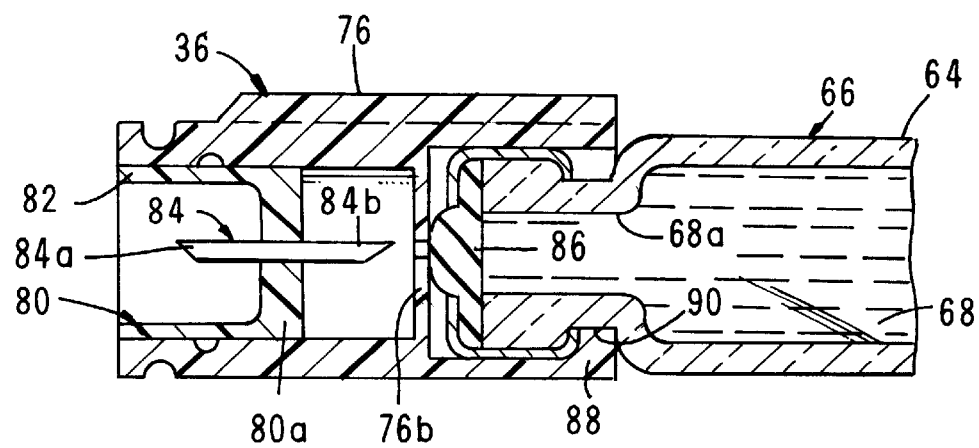
FIG. 3 is an enlarged, cross-sectional view taken along lines 3—3 of FIG. 1.
Figure 4:
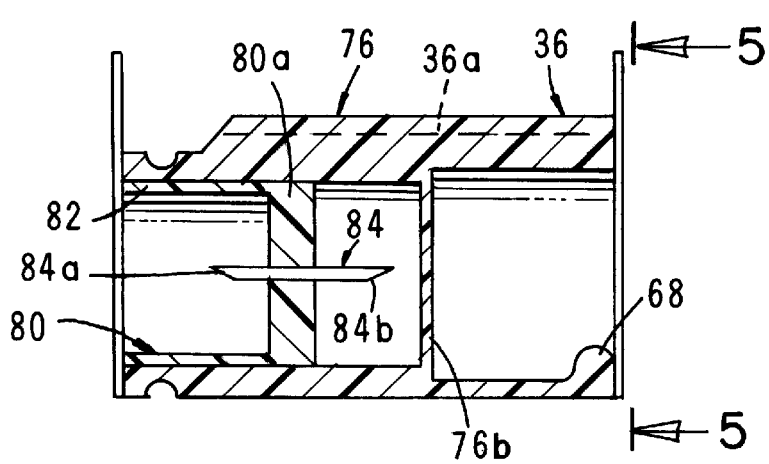
FIG. 4 is a cross-sectional view of one form of the polarity adapter component of the device shown before it has been affixed to a conventional medicament vial.
Figure 5:
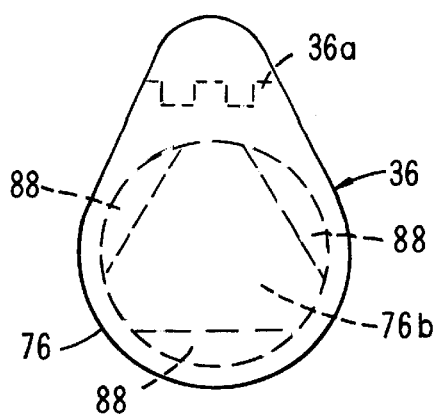
FIG. 5 is a view taken along lines 5—5 of FIG. 4.
Figure 6:
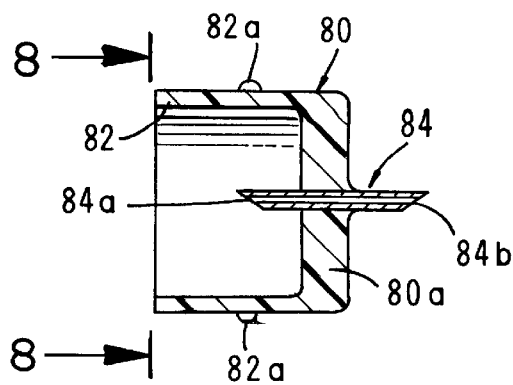
FIG. 6 is a side elevational, cross-sectional view of one form of the double ended cannula component of the invention which forms a pail of the polarity adapter assembly.
Figure 7:
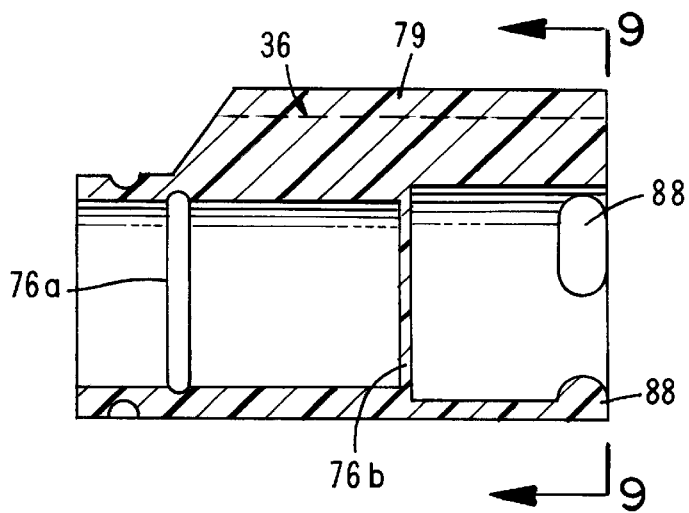
FIG. 7 is a side-elevational, cross-sectional view of one form of the connector housing of the polarity adapter of the invention.
Figure 8:
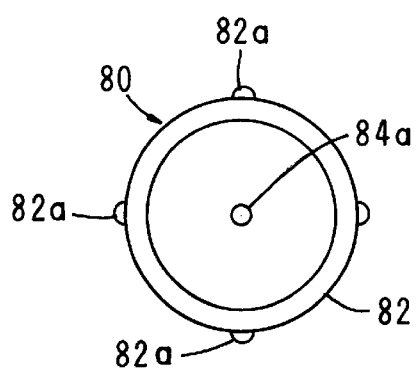
FIG. 8 is a view taken along lines 8—8 of FIG. 6.

Forming another very important aspect of the fluid delivery device of the present invention is the previously identified polarity adapter 36. This novel polarity adapter functions to interconnect the container or vial assembly 64 with the fluid delivery device housing 30. As best seen by referring to FIGS. 3 and 4, polarity adapter 36 includes a generally tubular shaped connector housing 76 which closely receives a novel double ended cannula component 80. As best seen in FIG. 6, component 80 has a partition wall 80a that supports a double-ended cannula 84 which is of the character shown in FIGS. 4 and 6. In addition to partition wall 80a, cannula component 80 includes a skirt portion 82 which is telescopically receivable within polarity adapter 36 in the manner shown in FIG. 4. As shown in FIGS. 3 and 10, hollow cannula 84 has a first end 84a for piercing first septum 62 of housing assembly 30 and a second end 84b for piercing a frangible dividing wall 76b and a pierceable septum 86 which forms a portion of vial assembly 64 and functions to sealably close the open end 68a of fluid chamber 68 (FIG. 3). Importantly, polarity adapter 36 is provided with a plurality of spaced-apart tongues 36a (FIG. 9) which, in a manner presently to be described, are receivable within a plurality of grooves 34a formed in sleeve 34 of housing assembly 30 (FIG. 1).

Provided proximate one end of polarity adapter 36 are circumferentially spaced-apart protuberances 88. When the polarity adapter is in interconnected with the container assembly 64 in the manner shown in FIG. 3, protuberances 88 snap into a groove 90 formed in the neck portion of the vial assembly. In this way, the polarity adapter is securely interconnected with the filled vial assembly 64 (see also FIG. 1). With this novel construction, when the assemblage made up of polarity adapter 36 and vial assembly 64 (FIG. 3) is inserted into first adapter sleeve 34 so that tongues 36a index with grooves 34a, skirt 82 of double ended cannula component 80 will be closely received over a hub 60a in the manner shown in FIG. 10. When an inward pressure is exerted on the vial assembly, the double-ended cannula component 80 will slide interiorly of connector housing 76 from the first position shown in FIG. 3 to the second position shown in FIG. 10. As the double-ended cannula component moves toward the second position, end 84b of cannula 84 will pierce second septum 86 and at the same time, first end 84a of cannula 84 will pierce first pierceable septum 62 which closes fill chamber 60. With the components in this mated condition, a fluid pathway is formed between chamber 68 of the vial assembly and chamber 60 of hub member 60a of the housing assembly 30. This sliding movement of double-ended cannula component 80 within connector housing 76 results when sleeve assembly 74 is inserted into receiving chamber 32 and is urged inwardly thereof. As shown in FIG. 1, sleeve assembly 74 includes a generally cross-shaped pusher means or pusher member 94 which engages plunger 70 upon sleeve assembly 74 being inserted into receiving chamber 32.

Figure 11:
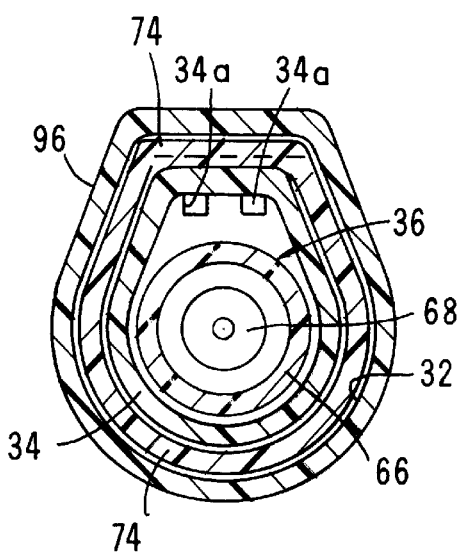
FIG. 11 is a cross-sectional view taken along lines 11—11 of FIG. 10.
Figure 12:
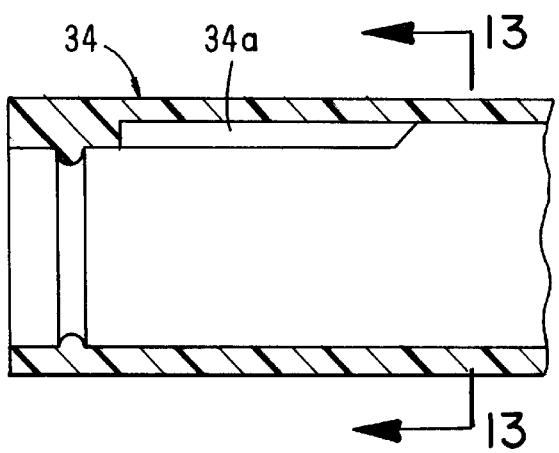
FIG. 12 is a fragmentary, cross-sectional view of the forward portion of one of the adapter sleeves of the fluid delivery device which telescopically receives the polarity adapter.

As best seen in FIGS. 1 and 11, receiving chamber 32 is defined by a truncated, generally tear-shaped liner 96 which forms a part of fluid device housing assembly 30. Formed proximate the outboard end of liner 96 is a resiliently deformable locking tab 96a (FIG. 1). As indicated in FIGS. 1 and 10, a plurality of longitudinally spaced-apart locking teeth 98 are formed on second adapter sleeve 74. With this construction, when sleeve 74 is telescopically inserted into receiving chamber 32, locking tab 96a will slide over the sloping surfaces of the locking teeth 98 until the sleeve 74 is seated within receiving chamber 32. At this point, locking tab 96a will spring into engagement with one of the radially outwardly extending faces of one of the locking teeth 98 thereby preventing removal of the adapter sleeve 74 from the receiving chamber 32.

As previously discussed, when the adapter sleeve 74 is urged inwardly of receiving chamber 32, the, pusher means, or pusher member 94, will engage plunger 70 urging the assemblage comprising the polarity adapter and vial assembly (FIG. 3) to move inwardly within sleeve of component 80 as the polarity adapter assembly mates over hub-like member 60a (FIG. 10). This, in turn, will cause component 80 to slide inwardly of the polarity adapter to a location where end 84b of cannula 84 engages septum 86 and where end 84a of the cannula is in engagement with septum 62. A continued inward force exerted on sleeve 74 will cause the cannula to pierce both septums thereby establishing fluid communication between vial chamber 68 and fill chamber 60.

It is to be noted that mating of polarity adapter with the fluid delivery device housing is only possible when the tongues 36a provided on the polarity adapter are in indexable alignment with the grooves 34a provided in adapter sleeve 34. If either the spacing, configuration or number of tongues 36a on sleeve 36 do not mate with the spacing, configuration and number of grooves 34a provided in sleeve 34 of the housing assembly 30 mating of the vial assembly with the housing is not possible. Accordingly, unless the polarity adapter and second sleeve 34 are of a compatible configuration, it is not possible to open a fluid communication path between chamber 68 of the vial assembly and fill chamber 60 of the fluid delivery device housing 30. Therefore, the erroneous filling of reservoir 38 with a fluid not compatible with the delivery profile of the housing 30 is positively prevented.

Figure 9:
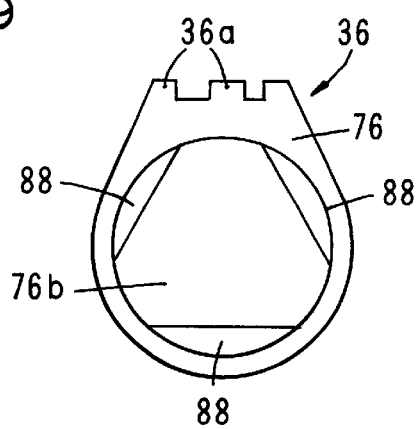
FIG. 9 is a view taken along lines 9—9 of FIG. 7.

It is also to be observed that both the first adapter sleeve 34 and the connector housing 36 of the polarity adapter are of the same truncated, generally tear-shaped configuration (FIG. 9). However, if the configuration of the polarity adapter does not match the configuration of the adapter sleeve 34, mating of the two components would not be possible. Because this unique configuration mating feature of the apparatus of the invention further positively prevents the erroneous filling of reservoir 38 with a medicament not compatible with the delivery profile of the delivery device. Further guarding against erroneous filling of reservoir 38 is the fact that second sleeve 74 is also of a trincated, generally tear-drop shape which is receivable only within the truncated, tear-drop shaped liner 96 that defines receiving chamber 32.

Figure 13:
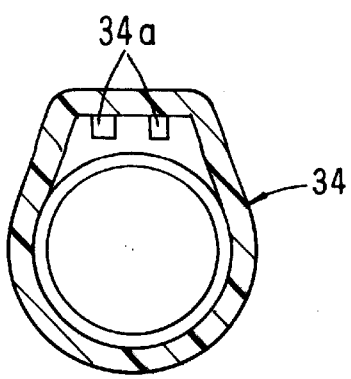
FIG. 13 is a cross-sectional view taken along lines 13—13 of FIG. 12.
Figure 18:
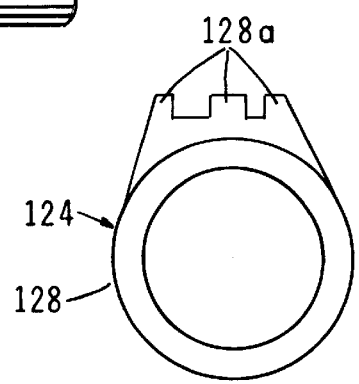
FIG. 18 is a view taken along lines 18—18 of FIG. 17.
Figures 20, 21:
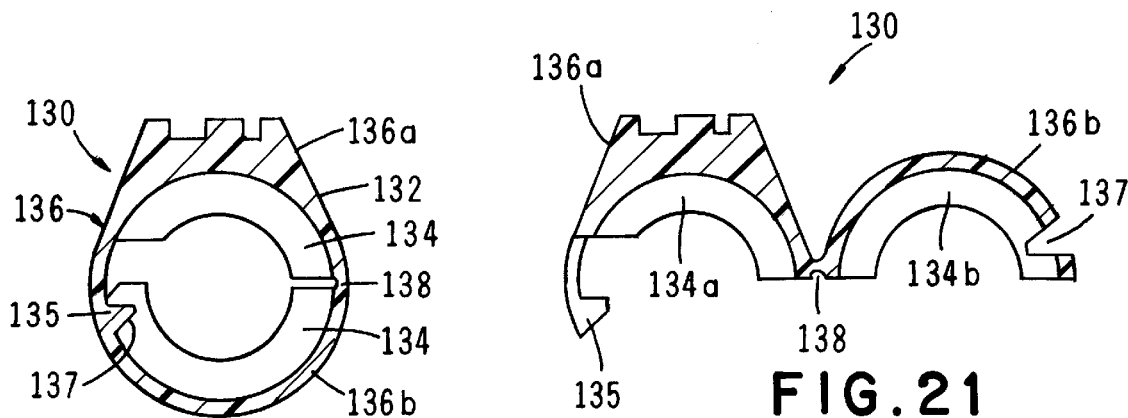
FIG. 20 is a cross-sectional view taken along lines 20—20 of FIG. 19.
FIG. 21 is a cross-sectional view of the polarity adapter illustrated in FIGS. 19 and 20, but shown in an open configuration.

In summary, it is apparent that, unless the polarity adapter is of the proper shape and has the proper number and arrangement of tongue components 36a, the polarity adapter cannot be used to mate a given vial assembly with a particular delivery device housing in the manner shown in FIGS. 13, 18 and 20. Accordingly, by tailoring the delivery device housing so that it can only receive polarity adapters of a particular configuration, the erroneous coupling of an improper vial assembly with the particular fluid delivery device being used is positively prevented.

Figure 14:
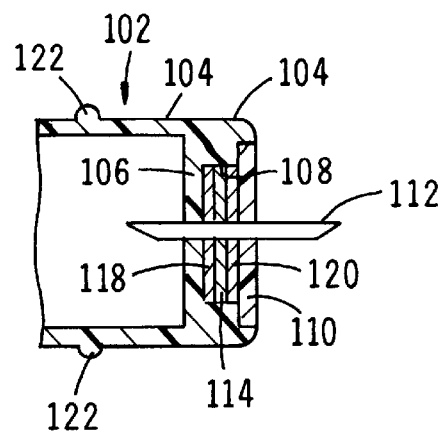
FIG. 14 is a side-elevational, cross-sectional view of an alternate form of the double-ended cannula component of the polarity adapter assembly of the invention.
Figure 15:
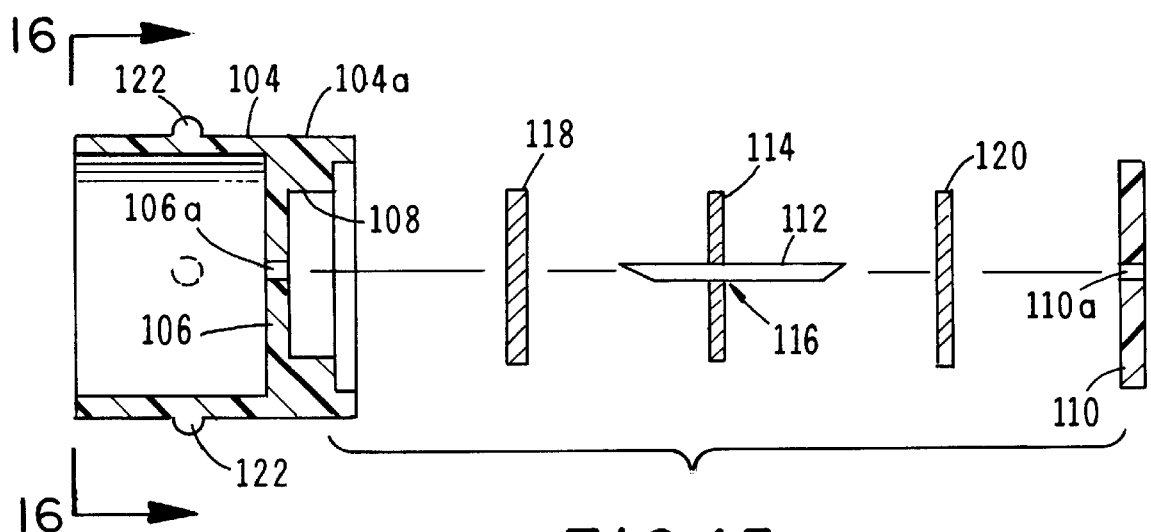
FIG. 15 is an exploded, side-elevational, cross-sectional view of the alternate form of double-ended cannula component shown in FIG. 14.
Figure 16:
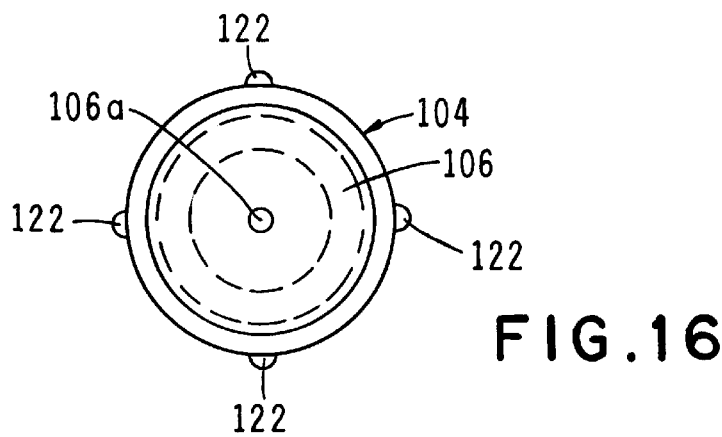
FIG. 16 is a view taken along lines 16—16 of FIG. 15.

Referring next to FIGS. 14 through 16, another form of polarity adapter assembly of the invention is there shown. This adapter assembly is similar in many respects to polarity adapter assembly 36, but the double ended cannula component, which is telescopically received within connector housing 36, is a different construction. More particularly, this component here includes a needle housing 102 that includes a generally cylindrically shaped body 104 having a partition wall 106. As best seen in FIG. 14, portion 104a of body 104 is counterbored to define a chamber 108 within which needle retaining plate 110 is mounted, which plate supports one end of a hollow, needle-like cannula 112. Cannula 112 is further supported by a disk-like member 114 to which the cannula is laser welded to form an assemblage 116 (FIG. 15). Assemblage 116 is mated with housing 102 in the manner shown in FIG. 14 so that one end of the cannula extends through an aperture 106a formed in partition wall 106 and the other end extends through an aperture 110a formed in support plate 110 (FIG. 15). Also received within chamber 108 and positioned on either side of member 114 are generally disk-shaped, elastomer seals 118 and 120. When support plate 110 is affixed to end 104a of body 104 in the manner shown in FIG. 14, elastomer seals 118 and 120 provide a leak-tight seal that prevents fluid leakage past cannula assemblage 116. As before, body 104 is provided with circumferentially spaced protuberances 122 which retain body 104 within connector housing 36.

Figure 17:
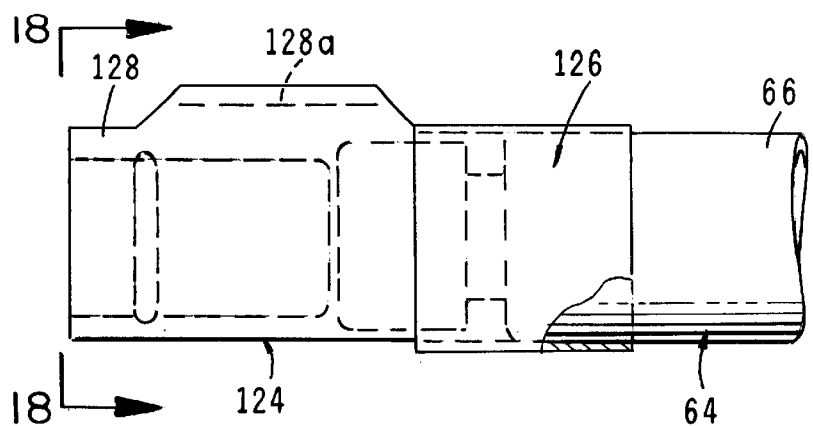
FIG. 17 is a side elevational view of still another form of polarity adapter of the invention shown affixed to a conventional medicament vial.

Turning to FIG. 17 still another form of tamper evident polarity adapter assembly of the invention is shown. This adapter assembly is also similar in many respects to polarity adapter assembly 36 and includes a generally tubular shaped connector housing 124 which closely receives the double-ended cannula component 80. In this particular form of adapter assembly, a plastic, heat shrink sleeve 126 is provided to fixedly interconnect the adapter housing 124 with the vial assembly 64. This novel sleeve 126 is placed over the rearward portion of the adapter housing and the forward portion of the vial assembly and then heated so as to shrink and closely conform to and securely interconnect together the adapter housing and the dial assembly. This novel construction provides a tamper evident connection which positively prevents undetected, unauthorized tampering with the assemblage prior to its interconnection with the delivery device.

As was the case with polarity adapter 36, adapter 124 functions to interconnect the container or vial assembly 64 with the fluid delivery device housing 30. For this purpose, adapter 124 includes a generally tubular shaped connector housing 128 which closely receives the previously described double-ended cannula component 80. As best seen in FIG. 18, connector housing 128 is provided with a plurality of spaced-apart tongues 128a which, as before, mate with grooves 34a provided in first adapter sleeve 34 when the polarity adapter is inserted into sleeve 34.

Figure 19:
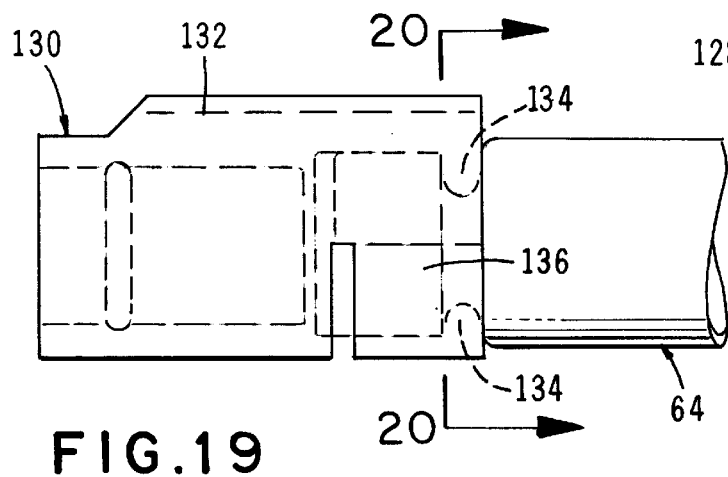
FIG. 19 is a side-elevational view of yet another form of polarity adapter of the invention shown affixed to a conventional medicament vial.

Referring to FIGS. 19 through 21, yet another form of tamper evident polarity adapter assembly of the invention is shown and generally identified by the numeral 130. This adapter assembly is also similar in many respects to polarity adapter assembly 36 and includes a generally tubular shaped connector housing 132 which closely receives the double-ended cannula component 80 in the manner previously described in connection with the embodiment shown in FIGS. 1 through 9. In this latest form of the adapter assembly, the connector housing which telescopically accepts the double-ended cannula component 80 is constructed in two parts, namely an annular shaped split ring portion 134 and an outer connector housing portion 136.

As best seen in FIG. 21, portion 136 comprises an upper segment 136a and a lower segment 136b which are uniquely connected by means of a living hinge 138. With this construction adapter assembly 130 can be moved from the open position shown in FIG. 21 to the closed vial engaging position shown in FIG. 20 wherein split ring 134 is closely received within groove 90 formed in the neck portion of the vial assembly 64. As indicated in FIGS. 20 and 21, portion 136a is provided with a hook-like element 135 which is adapted to lockably engage a generally "V" shaped opening 137 formed in split ring portion 134b. With this construction, when hook-like element 135 is snapped into locking engagement with opening 137 in the manner shown in FIG. 20, polarity adapter assembly 130 can be positively secured to the vial assembly. Once the polarity adapter is thus connected to the vial assembly any attempt to disconnect it from the vial from the polarity adapter will be at once evident because the adapter will be damaged to an extent that it cannot be suitably connected to another vial assembly.

Figure 27:
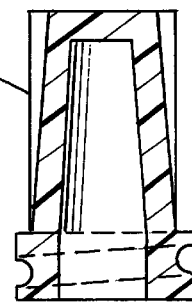
FIG. 27 is a side-elevational, cross sectional view, showing the construction of the closure cap of the invention that is used for sealably closing the outlet port of the fluid delivery device prior to use.
Figure 26:
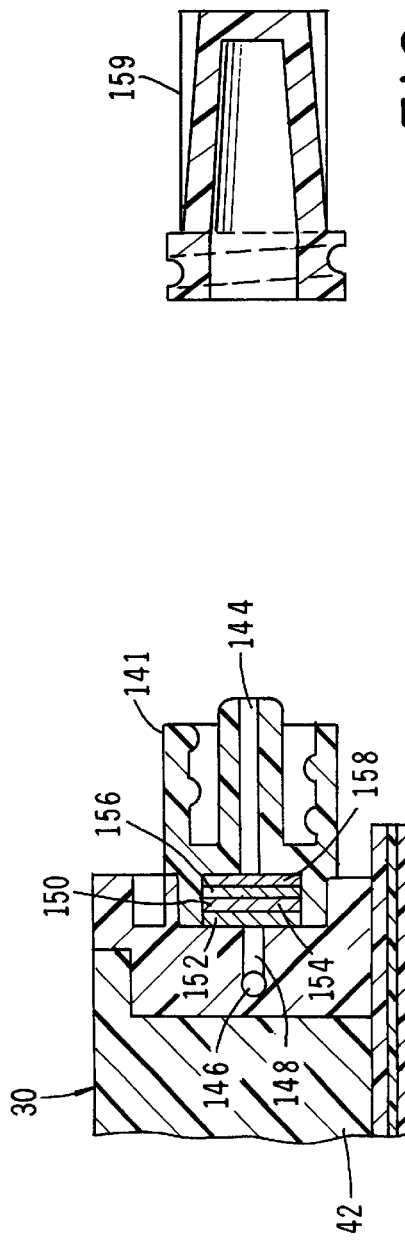
FIG. 26 is an enlarged, fragmentary, cross-sectional view of the outlet port and flow control portions of the embodiment of the invention shown in FIG. 24.

Connected to housing assembly 30 is an infusion means for infusing medicament to the patient. This infusion means here comprises a luer connector 141 having an outlet passageway 144 that is in communication with passageway 58 via a transverse passageway 146 a stub passageway 148 (FIG. 22) and a novel fluid flow control means that is disposed between outlet passageway 144 and stub passageway 148. As best seen in FIG. 26, this novel fluid flow control means here comprises an assemblage 150 made up of a porous distribution disk 152 for distributing fluid flowing from stub passageway 148 radially outwardly over a first filter element 154. The fluid, after being filtered by element 154 to remove any particulate matter therefrom, fluid flows through a porous rate control element 156 and then through a second filter element 158. Rate control element 156 is formed with a known porosity and functions to precisely control the rate of the fluid flow toward outlet passageway 144. Delivery luer connector 141 is of conventional construction so as to enable connection thereto of a conventional administration set of a character well known to those skilled in the art. Prior to use, the outboard end of the luer connector 141 is preferably covered with a closure cap 159 of the character shown in FIG. 27.

Referring now to FIGS. 28 through 32, yet another form of the fluid delivery device of the invention is there shown. This form of the invention is similar in many respects to that shown in FIGS. 1 through 7 and like numerals are used in FIGS. 28 through 32 to identify like components. As before, the device here comprises a housing assembly 30 having an elongated receiving chamber 32. The housing assembly 30 is substantially identical to that shown in FIGS. 1 through 7 and previously described herein. This alternate form of the invention also includes a first adapter sleeve 164 that is telescopically receivable within chamber 32 and a novel polarity adapter 166 (FIG. 29) that is, in turn, telescopically receivable within adapter sleeve 164 in the manner indicated in the drawings.

Figure 28:
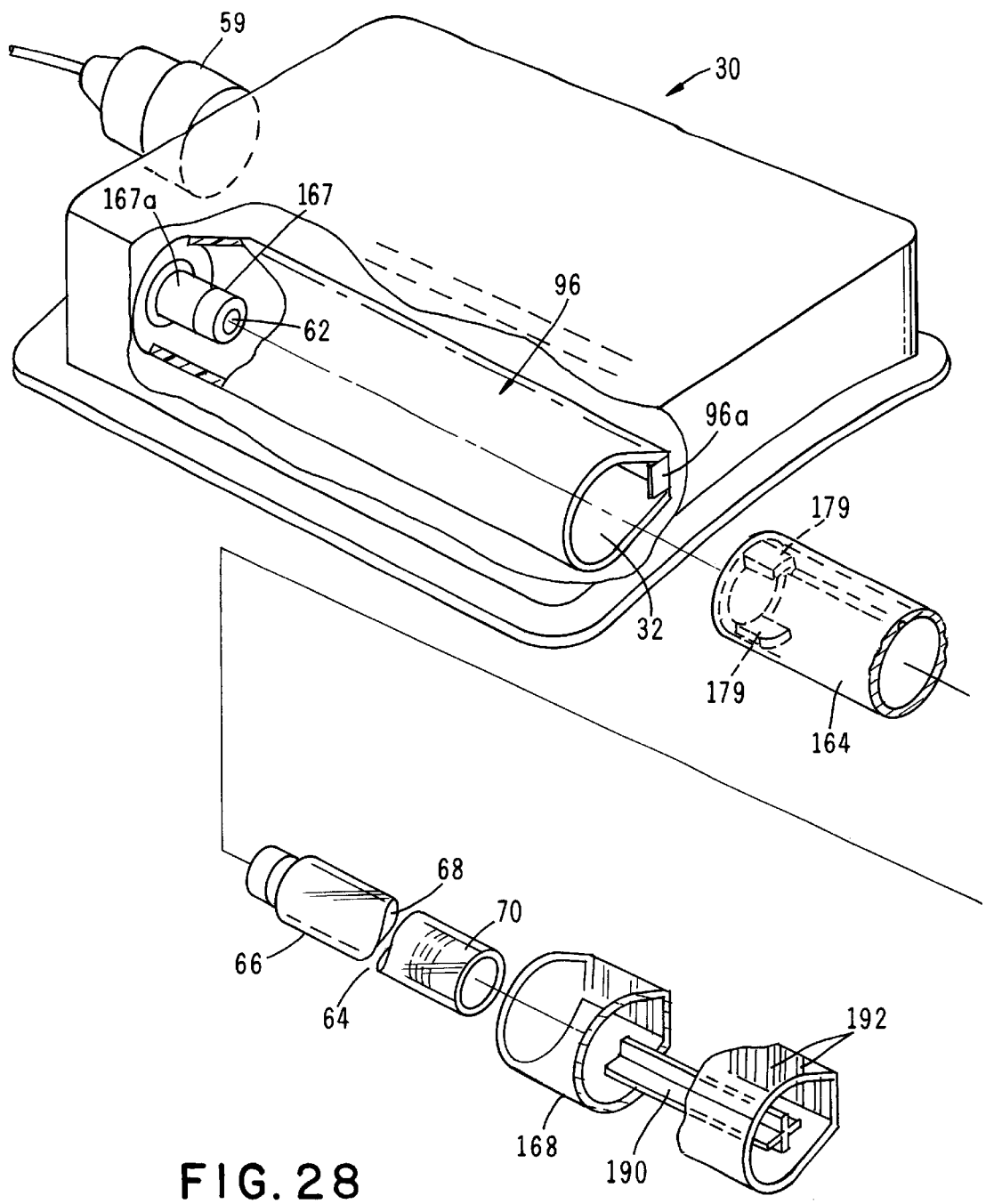
FIG. 28 is a generally perspective, exploded view of an alternate form of the delivery device of the present invention.
Figure 29:
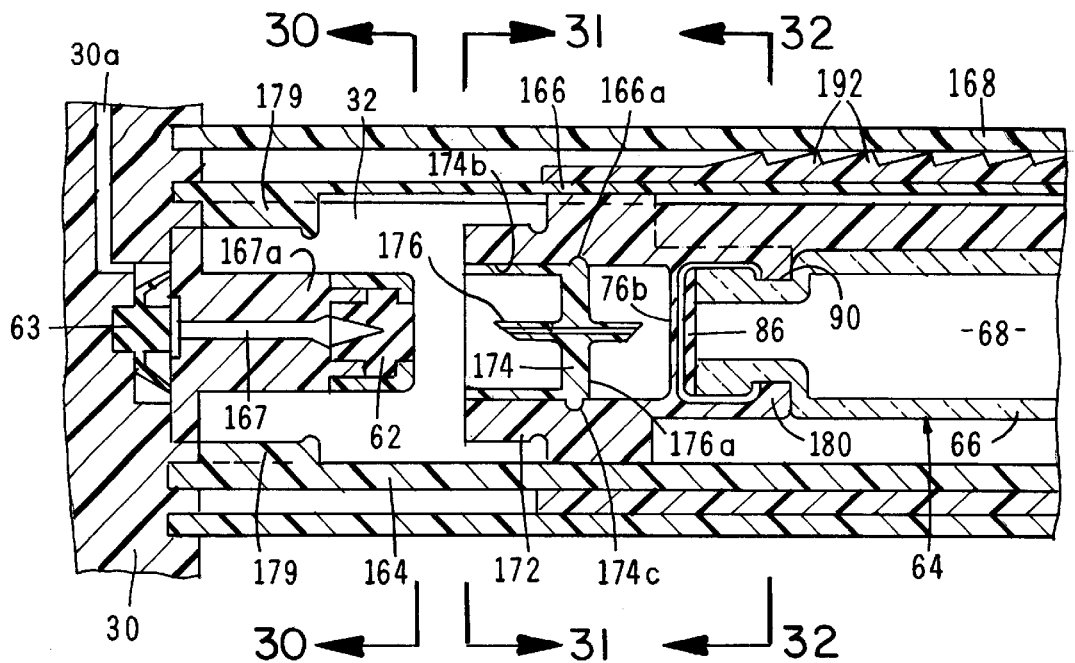
FIG. 29 is an enlarged, cross-sectional, fragmentary view, somewhat similar to FIG. 10, showing a portion of the fluid delivery device of this latest form of the invention illustrating the medicament vial connected to the housing of the delivery device by means of a polarity adapter of slightly different construction and showing the double-ended hollow cannula in position to simultaneously pierce both the vial septum and the delivery device septum
Figure 28A:
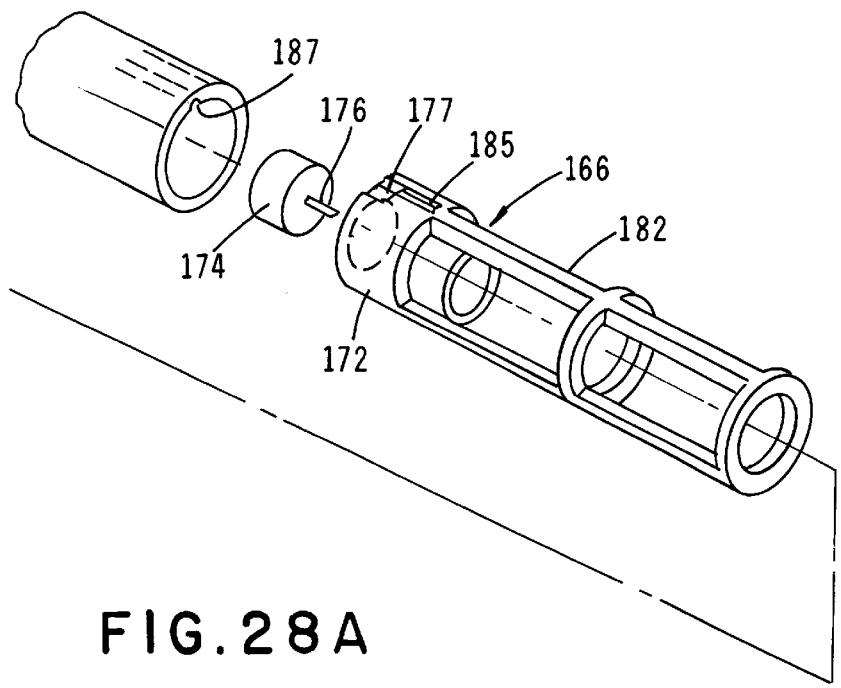
Figure 30:
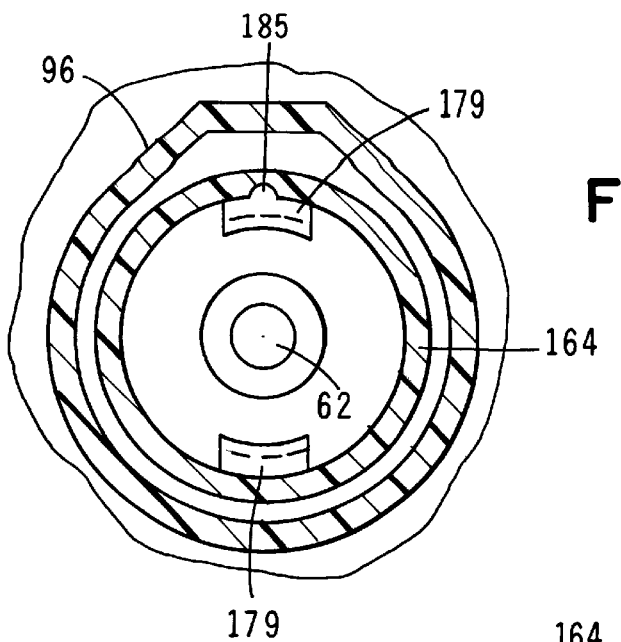
FIG. 30 is a cross-sectional view taken along lines 30—30 of FIG. 29.
Figure 31:
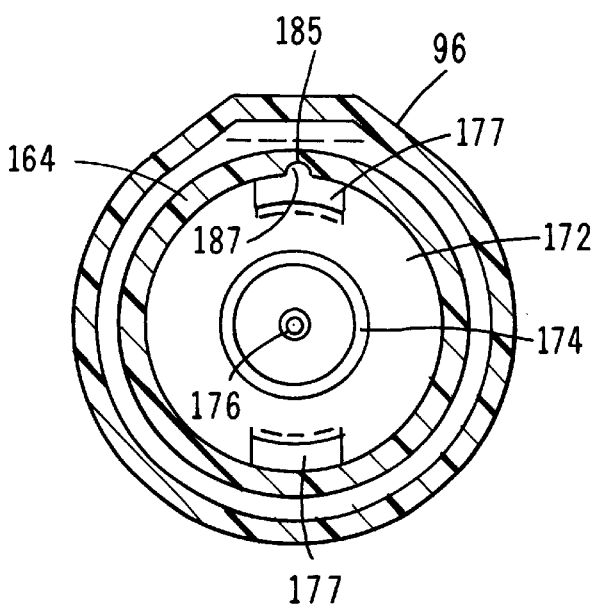
FIG. 31 is a cross-sectional view taken along lines 31—31 of FIG. 29.

As in the earlier described embodiments, housing assembly 30 includes a fluid reservoir for containing the medicinal fluids to be delivered to the patient. The fluid reservoir can be filled by fill means similar to that earlier described and communicates with substantially identical infusion means in the manner previously discussed herein. Housing assembly 30 also includes a fill chamber 167 which is closed by a first pierceable septum 62 (FIGS. 28 and 29). As before, fill chamber 167 is formed within a hub-like member 167a and is disposed within the receiving chamber 32 of housing assembly 30.

The fill means of this latest embodiment of the invention comprises a container assembly 64 which includes a conventional container, or vial 66 (FIG. 28). Formed within the body portion of vial 66 is a fluid chamber 68 within which a plunger 70 is movable from a first location to a second spaced-apart location. Vial assembly 66 is telescopically receivable within a second sleeve assembly 168, the configuration of which will presently be described.

As in the earlier described forms of the invention, the polarity adapter functions to interconnect the container or vial assembly 64 with the fluid delivery device housing 30. As best seen by referring to FIGS. 28, 29, and 31, the polarity adapter 166 here, includes a generally tubular shaped connector housing 172 which closely receives a novel double ended cannula component 174. As best seen in FIG. 29, component 174 has a partition wall 174a that supports a double-ended cannula 176 which is of the same character as previously described. In addition to partition wall 174a, cannula component 174 includes a skirt portion 174b which is telescopically receivable within connector housing 172 in the manner shown in FIG. 29. Skirt portion 174b includes a plurality of circumferentially spaced protuberances 174c which are receivable within a groove 166a formed in connector housing 172 and function to lock component 174 in position within housing 172. As before, hollow cannula 176 has a first end for piercing first septum 62 of housing assembly 30 and a second end for piercing a frangible dividing wall 76b and a pierceable septum 86 which forms a portion of vial assembly 64 and functions to sealably close the open end of fluid chamber 68 (FIG. 29). Importantly, connector housing 172 is provided with a plurality of spaced-apart cavities 177 (FIG. 31) which, in a manner presently to be described, are specially configured to receive a plurality of specially configured bosses 179 formed on sleeve 164 of housing assembly 172.

Figure 32:
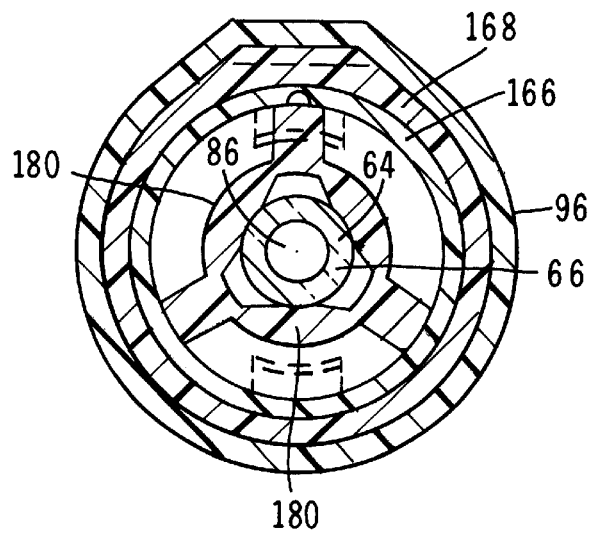
FIG. 32 is a cross-sectional view taken along lines 32—32 of FIG. 29.

Provided on connector housing 172 are circumferentially spaced-apart protuberances 180 (FIG. 32). When the polarity adapter is interconnected with the container assembly 64 in the manner shown in FIG. 29, protuberances 180 snap into a groove 90 formed in the neck portion of the vial assembly. In this way, the polarity adapter is securely interconnected with the filled vial assembly 64 and the vial assembly is supported within a vial cage 182 which is integrally formed with polarity adapter connector housing 172 (FIG. 28). Vial cage 182 can be sized to receive vials of various sizes, as for example, 1.5, and 3.0 milliliter volume vials.

With the novel construction described, when the assemblage made up of polarity adapter 166 and vial assembly 64 (FIG. 29) is inserted into first adapter sleeve 164 so that an indexing rib 185 formed on housing 172 indexes with a groove 187 formed in first adapter sleeve 164, skirt 174b of double ended cannula component 174 will be closely received over a hub 167a. When an inward pressure is exerted on the vial assembly, the double-ended cannula component 174 will slide interiorly of connector housing 172 and one end of the double-ended cannula component will pierce vial septum 86 and at the same time, the other end of cannula 176 will pierce the pierceable septum 62 which closes fill chamber 167. With the components in this mated condition, a fluid pathway is formed between chamber 68 of the vial assembly and chamber 167 of hub member 167a of the housing assembly 30. As in the earlier described embodiment, this sliding movement of double-ended cannula component 174 within connector housing 172 results when sleeve assembly 168 is inserted into receiving chamber 32 and is urged inwardly thereof., As shown in FIG. 28, sleeve assembly 168 includes a generally cross-shaped pusher means or pusher member 190 which engages plunger 70 upon sleeve assembly 1168 being inserted into receiving chamber 32.

As best seen in FIG. 28, receiving chamber 32 is once again defined by a truncated, generally tear-shaped liner 96 which forms a part of fluid device housing assembly 30. Formed proximate the outboard end of liner 96 is a resiliently deformable locking tab 96a (FIG. 28) which lockably engages one of a plurality of longitudinally spaced-apart locking teeth 192 formed on second sleeve assembly 168. With this construction, when sleeve 168 is telescopically inserted into receiving chamber 32, locking tab 96a will slide over the sloping surfaces of the locking teeth until the sleeve is seated within receiving chamber 32. At this point, locking tab 96a will spring into engagement with one of the radially outwardly extending faces of one of the locking teeth 192 thereby preventing removal of the sleeve assembly 168 from the receiving chamber 32.

It is to be noted that mating of polarity adapter with the fluid delivery device housing is only possible when the rib 185 provided on the polarity adapter is indexable with the grooves 187 provided in adapter sleeve 164. Additionally, the components can be fully mated only when bosses 179 are indexable with the cavities 177 formed in the polarity adapter housing 172. If either the spacing and configuration of rib 185 and groove 187 are not compatible, or if the spacing and configuration of bosses 179 are not compatible with the spacing and configuration of cavities 177, mating of the vial assembly with the housing is not possible. Accordingly, unless the mating components are of a compatible configuration, it is not possible to open a fluid communication path between chamber 68 of the vial assembly and fill chamber 167 of the fluid delivery device housing 30. Therefore, the erroneous filling of reservoir 38 with a fluid not compatible with the delivery profile of the housing 30 is positively prevented.

Figure 33:
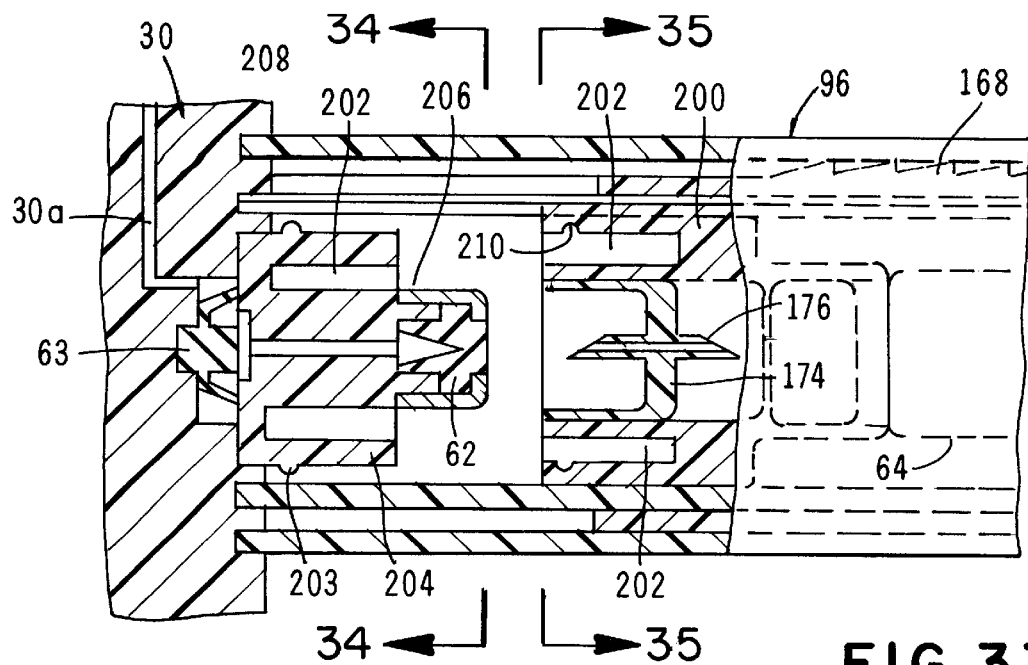
FIG. 33 is an enlarged, cross-sectional, fragmentary view, somewhat similar to FIG. 29, showing a portion of the fluid delivery device of still another form of the invention illustrating the medicament vial connected to the housing of the delivery device by means of a polarity adapter of slightly different construction and showing the double-ended hollow cannula in position to simultaneously pierce both the vial septum and the delivery device septum.
Figure 34:
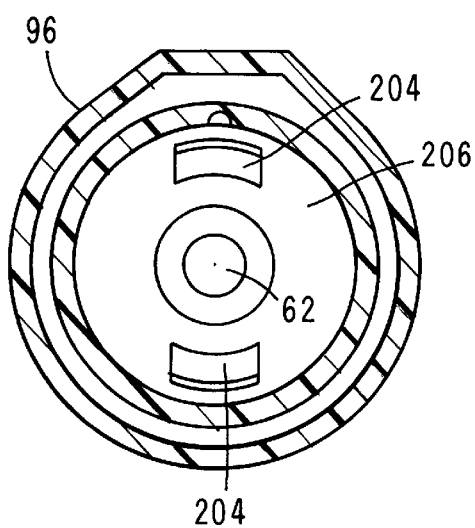
FIG. 34 is a cross-sectional view taken along lines 34—34 of FIG. 33.
Figure 35:
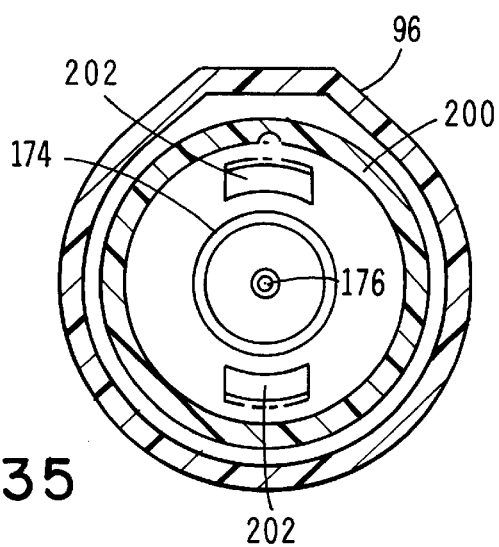
FIG. 35 is a cross-sectional view taken along lines 35—35 of FIG. 33.
Figure 36:
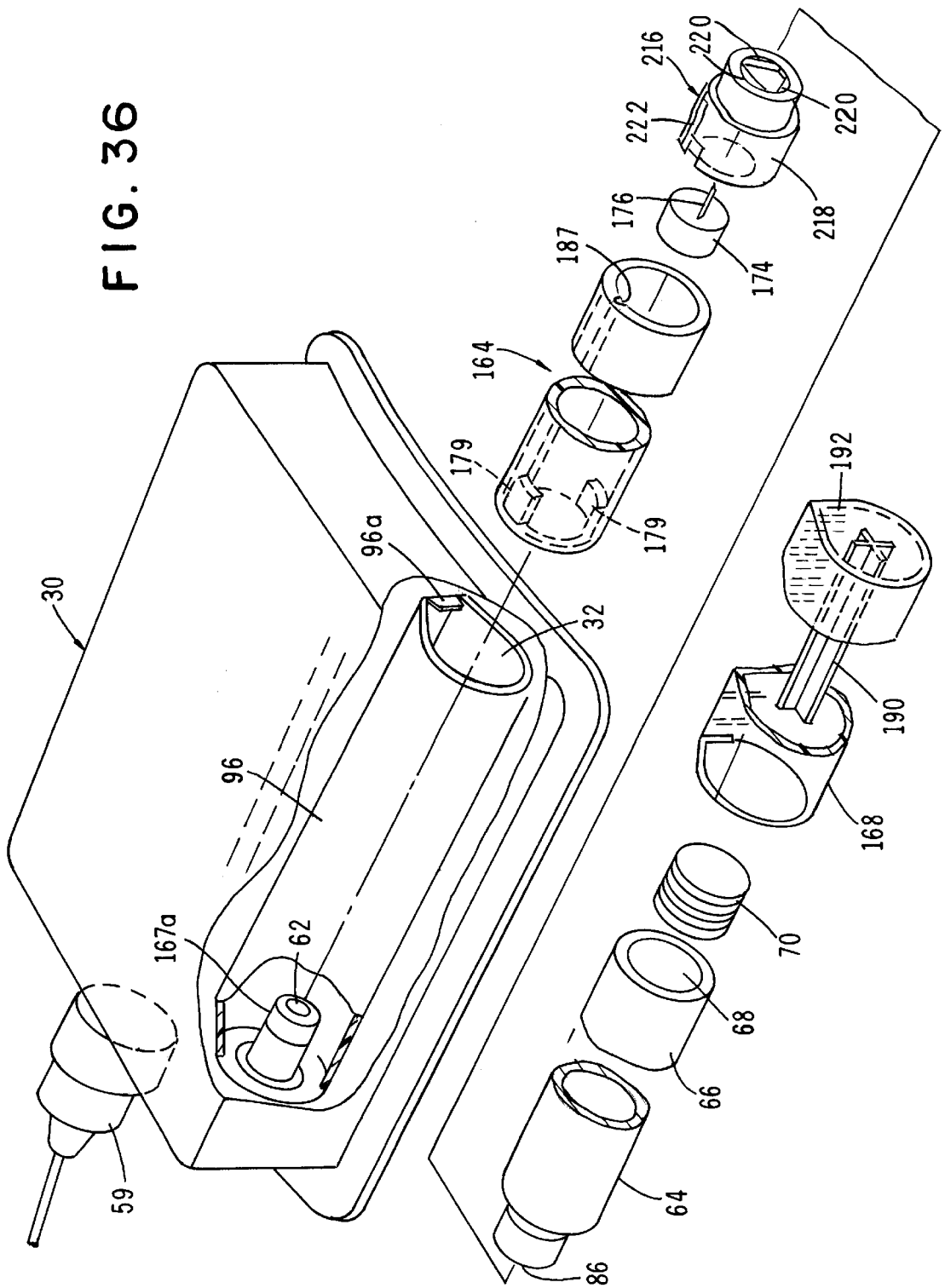
FIG. 36 is a generally perspective, exploded view of still another form of the delivery device of the present invention.
Figure 37:
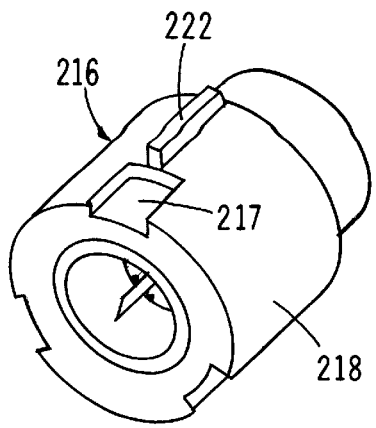
FIG. 37 is a generally perspective front view of the polarity adapter of the form of the invention shown in FIG. 36.

Referring next to FIGS. 33 through 35, another form of polarity adapter and housing assembly of the invention is there shown. This latest adapter assembly is similar in many respects to the earlier described polarity adapters, but the polarity adapter 200 is uniquely configured to include a pair of spaced apart cavities 202 that are configured to telescopically receive spaced bosses 204 formed on a fill chamber assembly 206 that is connected to housing assembly 30. Protuberance 208 formed on assembly 206 engage a groove 210 formed in the polarity adapter to lock the components together after being mated. Once again unless the polarity adapter is of the proper shape and has the proper number and spacing of cavities 202, it cannot be used to mate a given vial assembly with a particular delivery device housing. Accordingly, by tailoring the delivery device housing so that it can only receive polarity adapters of a particular configuration, the erroneous coupling of an improper vial assembly with the particular fluid delivery device being used is positively prevented.

Turning next to FIGS. 36 through 42, still another embodiment of the fluid delivery device of the invention is there shown. This form of the invention is quite similar to that shown in FIGS. 28 through 32 and like numerals are used in FIGS. 36 through 42 to identify like components. More particularly, the device comprises a housing assembly 30 having an elongated receiving chamber 32. The housing assembly 30 is substantially identical to that shown in FIGS. 28 through 32 and is the same construction and operation as that previously described. This alternate form of the invention also includes a first adapter sleeve 164 that is telescopically receivable within chamber 32 and a novel polarity adapter 216 (FIGS. 36, 37, and 38) that is, in turn, telescopically receivable within adapter sleeve 164 in the manner indicated in the drawings.

Figure 39:
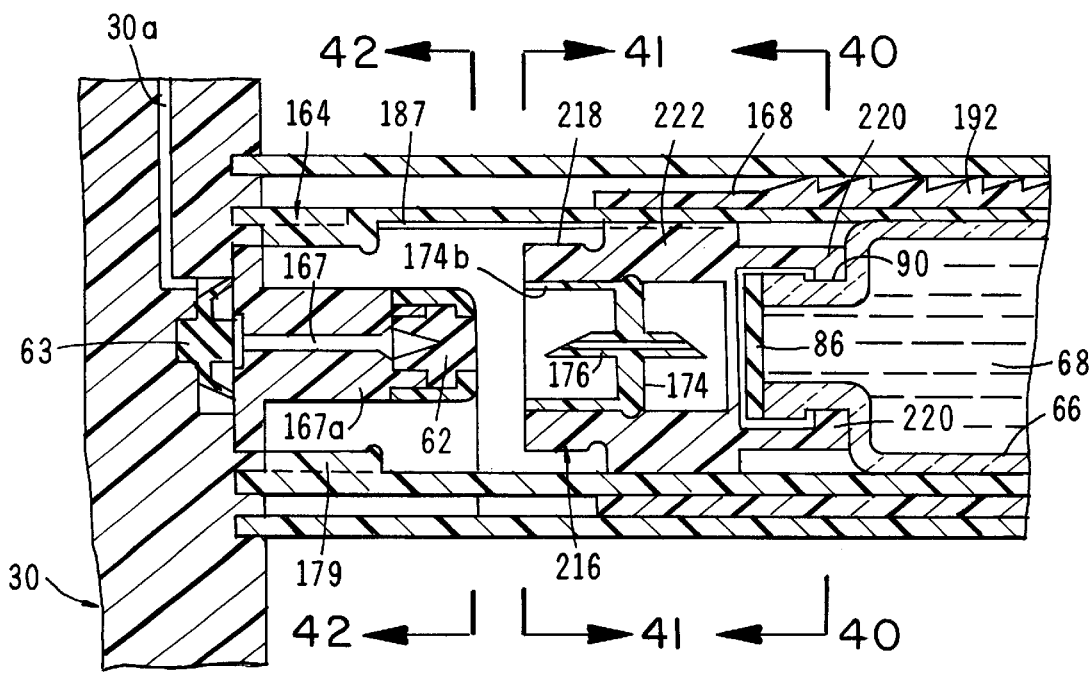
FIG. 39 is an enlarged, cross-sectional view, somewhat similar to FIG. 29, showing a portion of the fluid delivery device of this latest form of the invention illustrating the medicament vial connected to the housing of the delivery device by means of a polarity adapter of slightly different construction and showing the double-ended hollow cannula in position to simultaneously pierce both the vial septum and the delivery device septum.
Figure 40:
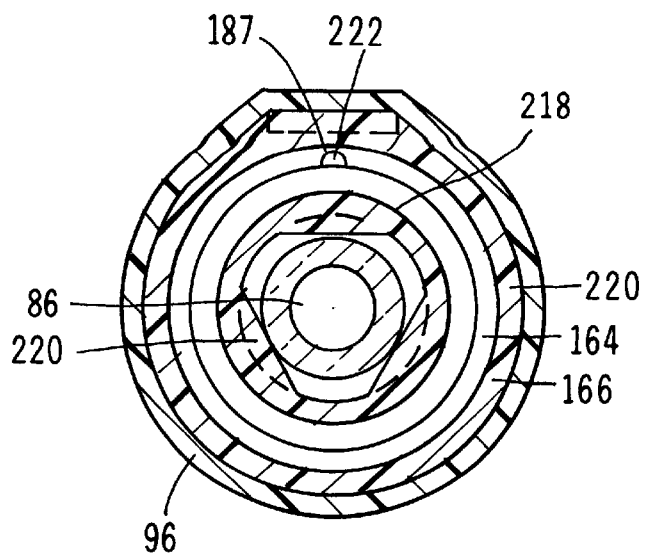
FIG. 40 is a cross-sectional view taken along lines 40—40 of FIG. 39.
Figure 41:
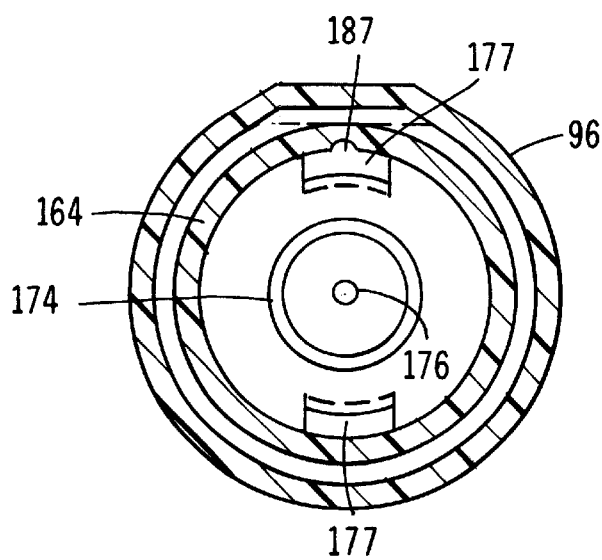
FIG. 41 is a cross-sectional view taken along lines 41—41 of FIG. 39.
Figure 42:
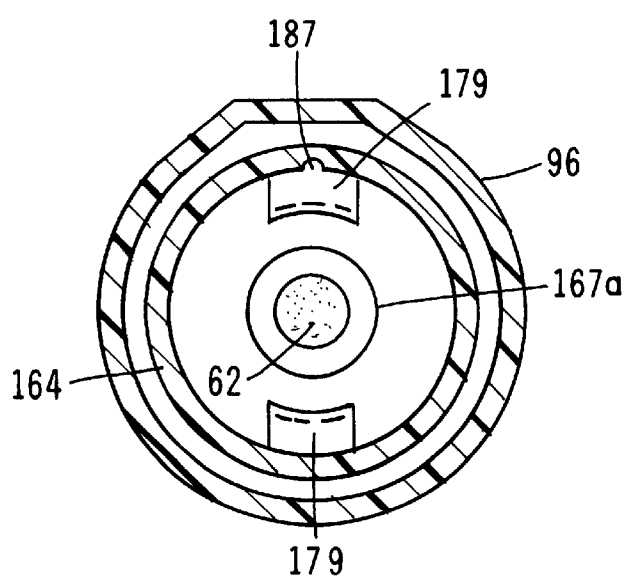
FIG. 42 is a cross-sectional view taken along lines 42—42 of FIG. 39.

The fill means of this latest embodiment of the invention is identical to that previously described and comprises a container assembly 64 which includes a conventional container, or vial 66 (FIG. 39). Formed within the body portion of vial 66 is a fluid chamber 68 within which a plunger 70 is movable from a first location to a second spaced-apart location. Vial assembly 66 is telescopically receivable within a second sleeve assembly, which is identical in construction and operation to sleeve assembly 168.

The polarity adapter 216 of this latest embodiment of the invention once again functions to interconnect the container or vial assembly 64 with the fluid delivery device housing 30, but is of a slightly different construction in that the vial cage component has been eliminated. As before, the polarity adapter 216 includes a generally tubular shaped connector housing 218 which closely receives the double ended cannula component 174, which of identical construction to that previously described.

Figure 38:
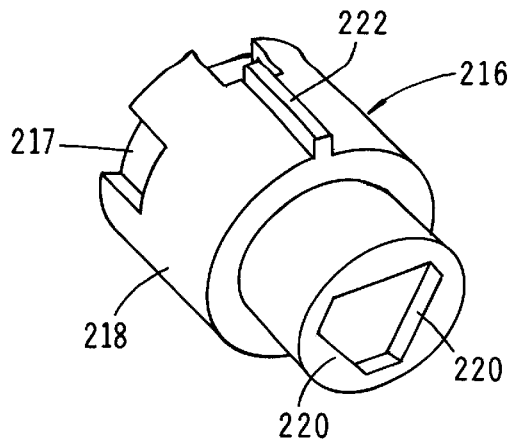
FIG. 38 is a generally perspective rear view of the polarity adapter.

Provided on connector housing 218 are circumferentially spaced-apart protuberances 220 (FIG. 38). When the polarity adapter is in interconnected with container 66 in the manner shown in FIG. 39, protuberances 220 snap into a groove 90 formed in the neck portion of the vial assembly. In this way, the polarity adapter is securely interconnected with the filled vial assembly 64 and the assembly thus formed can be inserted into first adapter sleeve 164 so that an indexing rib 222 formed on housing 218 indexes with a groove 187 formed in first adapter sleeve 164. As the assembly is moved inwardly, skirt 174b of double ended cannula component 174 will be closely received over a hub 167. When an inward pressure is exerted on the vial assembly, the double-ended cannula component will slide interiorly of connector housing 218 and one end of the double-ended cannula component will pierce vial septum 86 and at the same time, the other end of cannula 176 will pierce the pierceable septum 62 which closes fill chamber 167. With the components in this mated condition, a fluid pathway is formed between chamber 68 of the vial assembly and chamber 167 of hub member 167a of the housing assembly 30. As in the earlier described embodiment, this sliding movement of double-ended cannula component 174 within connector housing 218 results when sleeve assembly 168 is inserted into receiving chamber 32 and is urged inwardly thereof. As before, sleeve assembly 168 includes a generally cross-shaped pusher means or pusher member 190 which engages plunger 70 upon sleeve assembly 168 being inserted into receiving chamber 32.

As indicated in FIG. 39, the vial cage is not needed in this latest embodiment of the invention since a larger 5 ml vial is used which snugly fits into adapter sleeve 164.

As in the earlier described embodiments, mating of polarity adapter with the fluid delivery device housing is only possible when the rib 222 provided on the polarity adapter is indexable with the grooves 187 provided in adapter sleeve 164. Additionally, the components can be fully mated only when bosses 179 formed on sleeve 164 are indexable with the cavities 217 formed in the polarity adapter housing 218. If either the spacing and configuration of rib 222 and groove 187 are not compatible, or if the spacing and configuration of bosses 179 are not compatible with the spacing and configuration of cavities 217, mating of the vial assembly with the housing is not possible.

Figure 43:
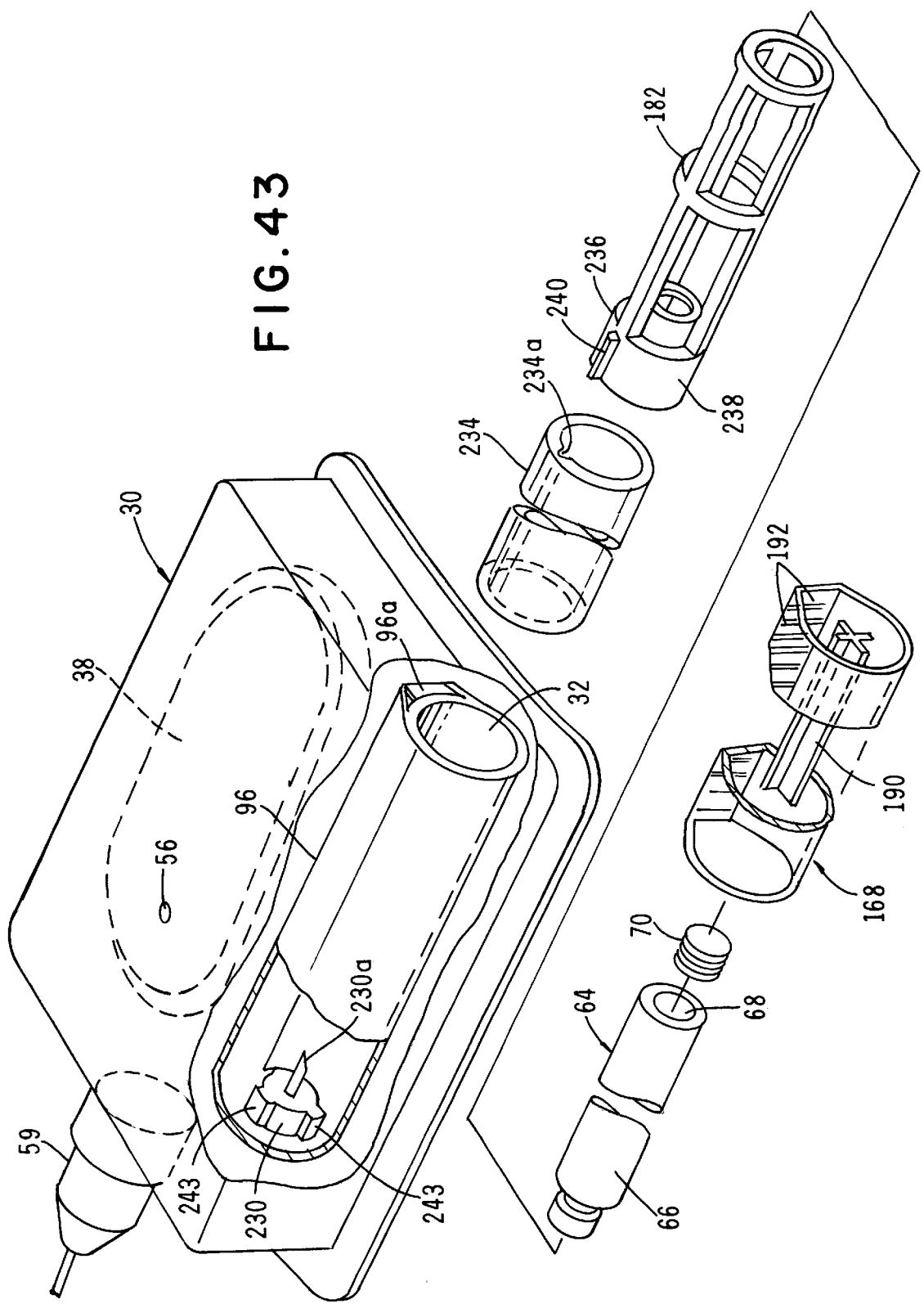
FIG. 43 is a generally perspective, exploded view of yet another alternate form of the delivery device of the present invention.
Figure 44:
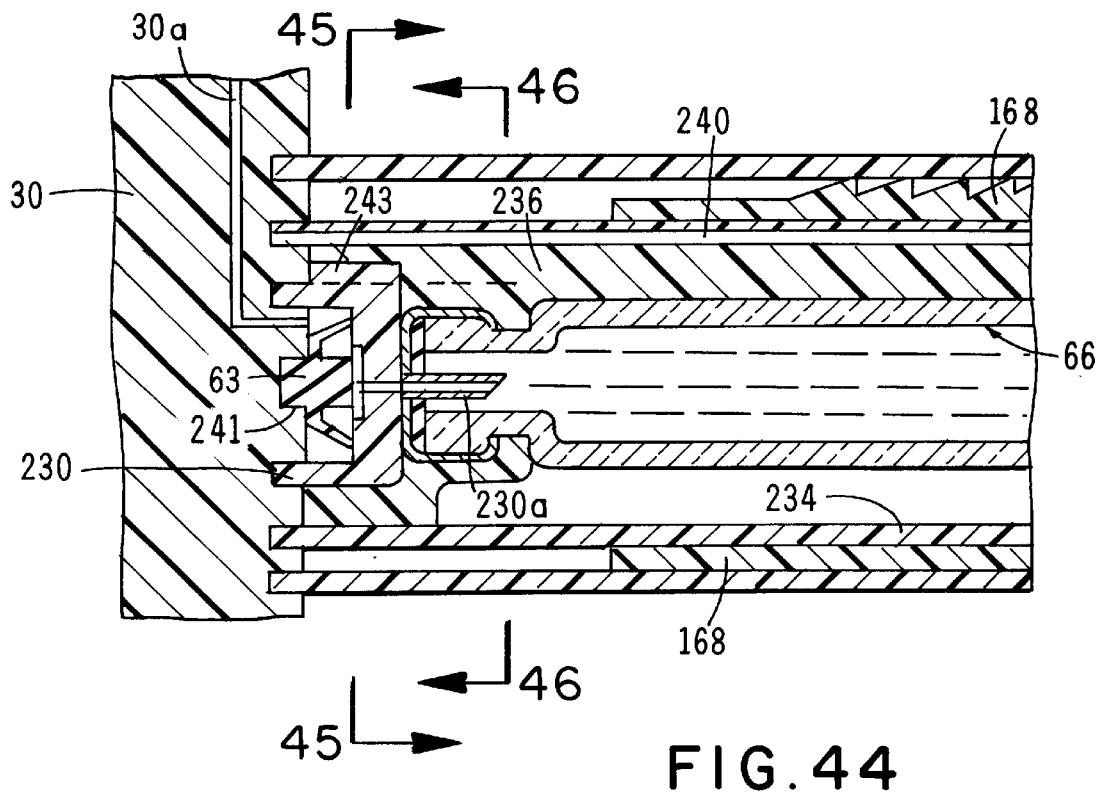
FIG. 44 is an enlarged, cross-sectional, fragmentary view, showing a portion of the fluid delivery device of this latest form of the invention illustrating the medicament vial connected to the housing of the delivery device by means of a polarity adapter of a different construction that does not include the double-ended hollow cannula component shown in the earlier figure drawings, but does include the vial cage for supporting the smaller diameter vials.
Figure 45:
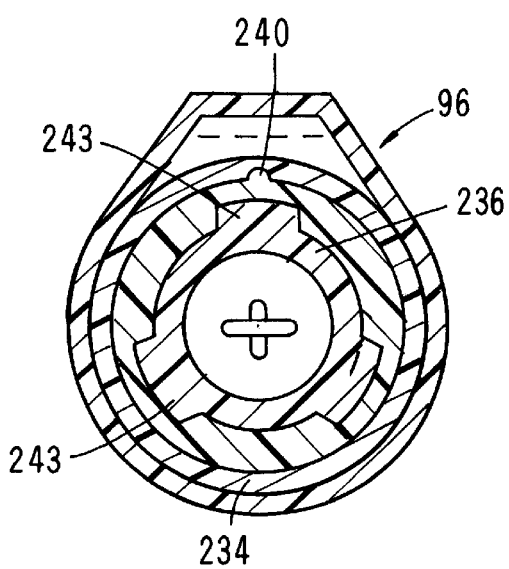
FIG. 45 is a cross-sectional view taken along lines 45—45 of FIG. 44.
Figure 46:
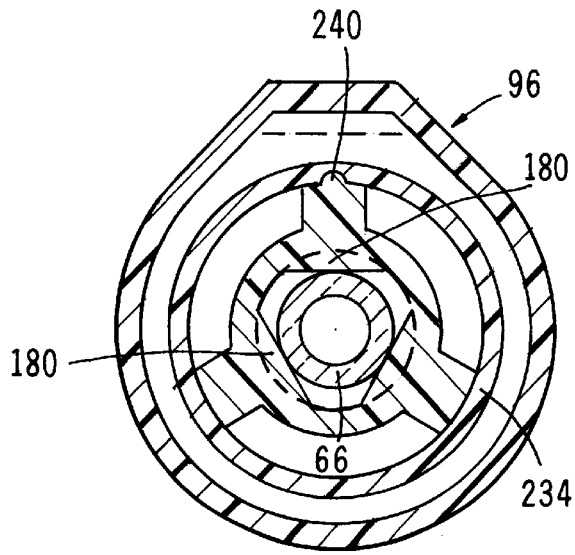
FIG. 46 is a cross-sectional view taken along lines 46—46 of FIG. 44.
Figure 48:
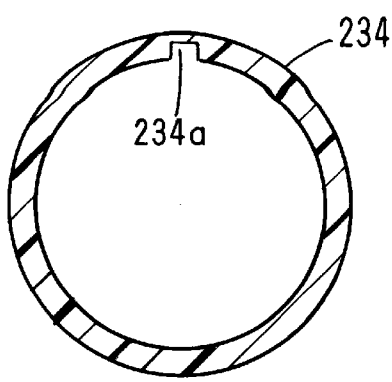
FIG. 48 is a cross-sectional view taken along lines 48—48 of FIG. 47.
Figure 49:
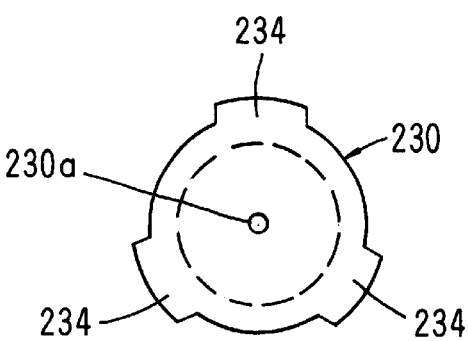
FIG. 49 is a cross-sectional view taken along lines 49—49 of FIG. 47.

Referring now to FIGS. 43 through 51, yet another embodiment of the fluid delivery device of the invention is there shown. This form of the invention is similar in many respects to that shown in FIGS. 28 through 32 save that the double ended cannula component of the polarity adapter has been replaced by a needle adapter 230 that is connected to housing assembly 30 and takes the place of hub-like member 167a. Because of the similarities of this latest embodiment to that shown in FIGS. 28 through 32 like numerals are used in FIGS. 43 through 51 to identify like components. As before, housing assembly 30 includes an elongated receiving chamber 32 that is formed by uniquely configured liner 96 and save for needle adapter 230 housing assembly 30 is substantially identical to that shown in FIGS. 1 through 7 and previously described herein. This alternate form of the invention also includes a first adapter sleeve 234 that is telescopically receivable within chamber 32 and a somewhat different polarity adapter 236 (FIG. 44).

The fill means of this latest embodiment of the invention once again comprises a container assembly 64 which includes a conventional container, or vial 66 (FIG. 43). Formed within the body portion of vial 66 is a fluid chamber 68 within which a plunger 70 is movable from a first location to a second spaced-apart location. Vial assembly 66 is telescopically receivable within a second sleeve assembly 168 which is of the configuration previously described.

As before, polarity adapter 236 functions to interconnect the container or vial assembly 64 with the fluid delivery device housing 30, but in this instance, mates with the novel needle adapter 230. Needle adapter 230 includes a hollow needle 230a that communicates with the fluid delivery device reservoir via check valve 63 and inlet passageway 30a. Polarity adapter 236 here includes a generally tubular shaped connector housing 238 which includes a longitudinally extending indexing rib or protuberance 240.

Figure 50:
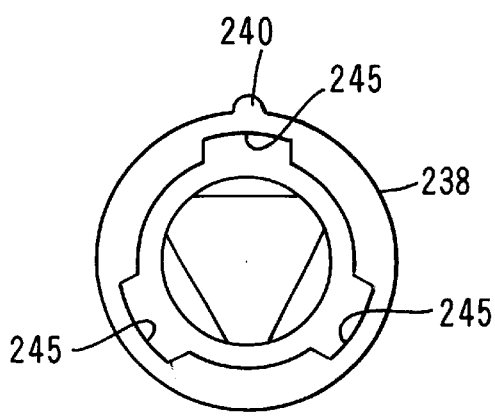
FIG. 50 is a cross-sectional view taken along lines 50—50 of FIG. 47.
Figure 51:
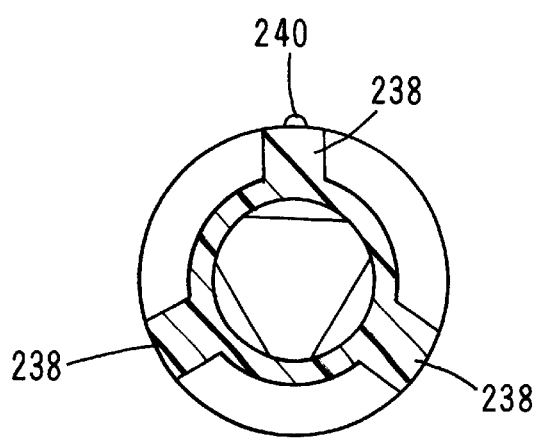
FIG. 51 is a cross-sectional view taken along lines 51—51 of FIG. 47.
Figure 52:
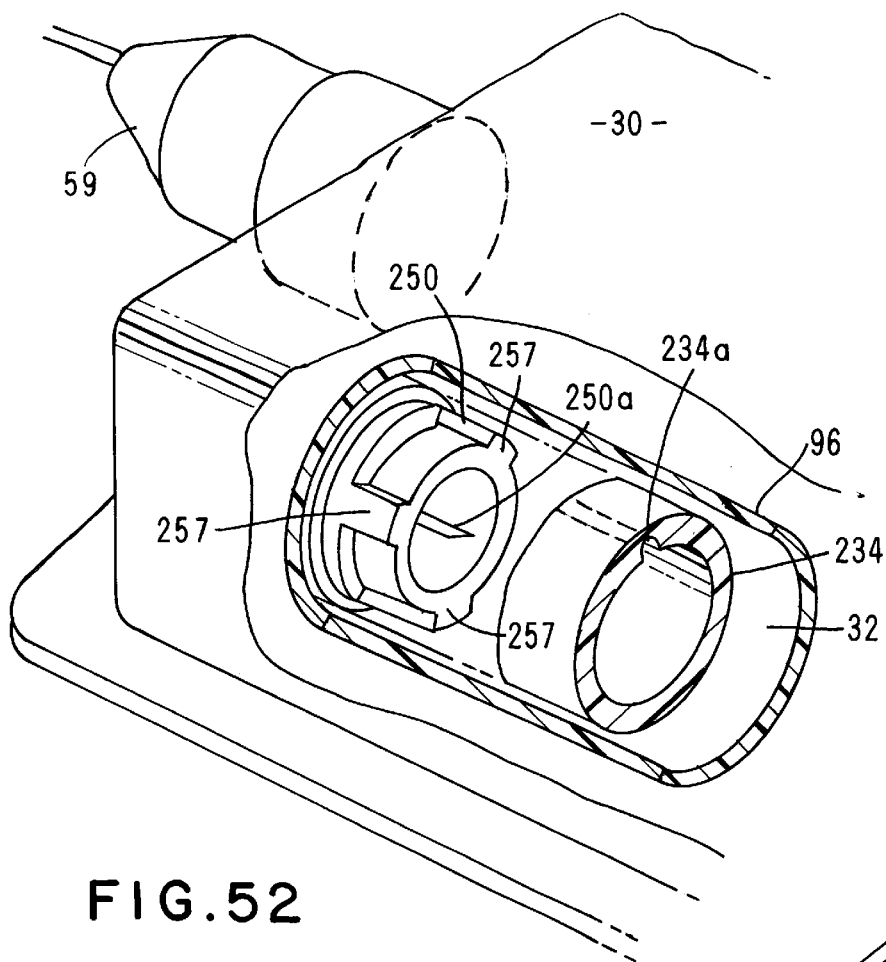
FIG. 52 is a generally perspective, fragmentary view, showing a portion of the fluid delivery device of still another form of the invention illustrating the configuration of the receiving chamber of the housing of the delivery device which is adapted to receive a polarity adapter of a slightly different construction.

Hollow needle 230a has a first end that pierces pierceable septum 86 of vial assembly 64 and a second end in fluid communication with a fill chamber 241 that houses check valve 63. Importantly, needle adapter 230 is provided with a plurality of circumferentially spaced bosses 243 which, in a manner presently to be described, are specially configured to be received within a plurality of circumferentially spaced cavities 245 formed in housing 238 of polarity adapter 236 (FIG. 50).

As in the earlier described embodiment, when the polarity adapter is securely interconnected with the filled vial assembly 64 in the manner previously described, the vial assembly is supported within a vial cage 182 which is integrally formed with polarity adapter connector housing 238 (FIG. 43). As before, vial cage 182 can be sized to receive vials of a number of different sizes, as for example, 1.5 and 3.0 volume vials.

With the novel construction described, when the assemblage made up of polarity adapted 236 and vial assembly 64 (FIG. 44) is inserted into first adapter sleeve 234 so that an indexing rib 240 formed on housing 238 indexes with a groove 234a formed in first adapter sleeve 234 and when an inward pressure is exerted on the vial assembly, the first end of hollow needle 230a will pierce vial septum 86. This opens a fluid pathway between chamber 68 of the vial assembly and chamber 241 of needle adapter 230. A continued inward movement of the vial assembly will cause the fluid contained within the vial to flow past check valve 63, into passageway 30a and finally into reservoir 38 via inlet port 56.

It is to be noted that mating of the polarity adapter of this latest form of the invention with the fluid delivery device housing is only possible when the rib 240 provided on the polarity adapter is indexable with the grooves 234a provided in adapter sleeve 234. Additionally, the components can be fully mated only when bosses 243 of the needle adapter are indexable with the cavities 245 formed in the polarity adapter housing 236.

Figure 53:
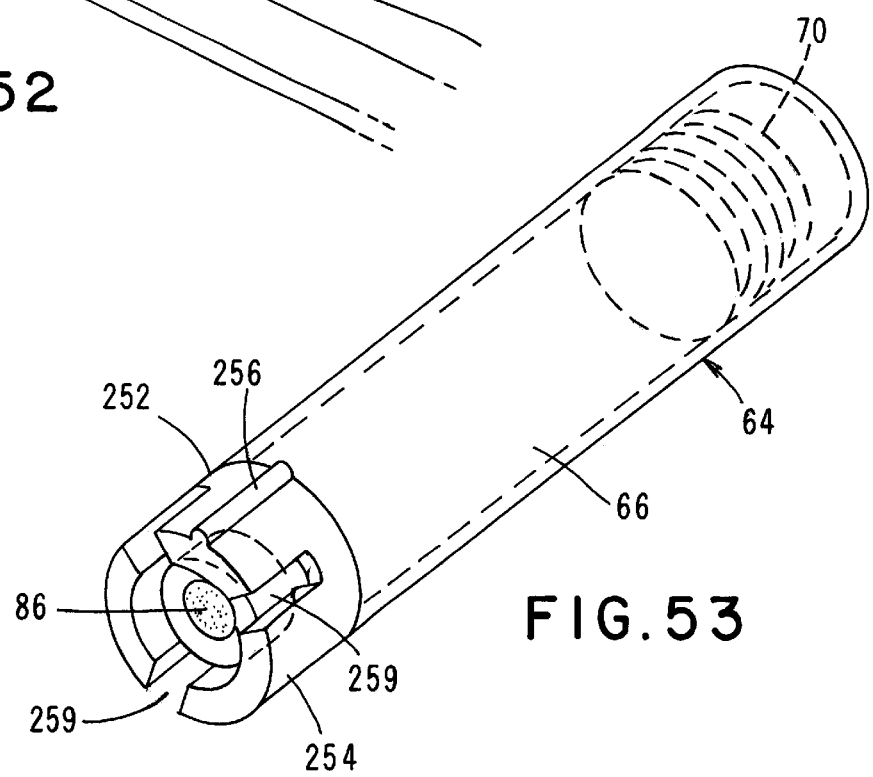
FIG. 53 is a generally perspective view of the polarity adapter and vial assembly construction that is receivable within the receiving chamber of the housing shown in FIG. 52.

Turning next to FIGS. 52 through 57, still another embodiment of the fluid delivery device of the invention is there shown. This form of the invention is quite similar to that shown in FIGS. 43 through 51 and, once again, the double ended cannula component of the polarity adapter has been replaced by a needle adapter 250 that is connected to housing assembly 30. Because of the similarities of this latest embodiment to that shown in FIGS. 43 through 51 like numerals are used in FIGS. 52 through 57 to identify like components. As before, housing assembly includes an elongated receiving chamber 32 that is formed by uniquely configured liner 96 and save for needle adapter 250 housing assembly 30 is substantially identical to that shown in FIGS. 1 through 7 and previously described herein. In this alternate form of the invention, the needle adapter, while similar in function to needle adapter 230 is adapted to be telescopically received directly within a somewhat differently configured polarity adapter 252 (FIGS. 53 and 57).

The fill means of this latest embodiment of the invention once again comprises a container assembly 64 which includes a conventional container, or vial 66 (FIG. 53). Formed within the body portion of vial 66 is a fluid chamber 68 within which a plunger 70 (FIG. 53) is movable from a first location to a second spaced-apart location. Vial assembly 66 is telescopically receivable within a second sleeve assembly 234 which is of the configuration previously described.

As before, polarity adapter 252 functions to interconnect the container or vial assembly 64 with the fluid delivery device housing 30, but in this instance, mates with the novel needle adapter 250 and does not include the vial cage 182 Needle adapter 250 includes a hollow needle 250a that communicates with the fluid delivery device reservoir via check valve 63 and inlet passageway 30a. Polarity adapter 252 here includes a generally tubular shaped connector housing 254 which includes a longitudinally extending indexing rib or protuberance 256.

As before, hollow needle 250a has a first end that pierces pierceable septum 86 of vial assembly 64 and a second end in fluid communication with a fill chamber 241 that houses check valve 63. Importantly, needle adapter 250 is provided with a plurality of circumferentially spaced bosses 257 which are specially configured to be received within a plurality of circumferentially spaced cavities 259 formed in housing 254 of polarity adapter 252 (FIG. 53).

In this latest embodiment, when the assemblage made up of polarity adapter 252 and vial assembly 64 (FIG. 53) is inserted into first adapter sleeve 234 so that an indexing rib 256 formed on housing 254 indexes with a groove 234a formed in first adapter sleeve 234 and when an inward pressure is exerted on the vial assembly, the first end of hollow needle 250a will pierce vial septum 86. This opens a fluid pathway between chamber 68 of the vial assembly and chamber 241 (FIG. 57). A continued inward movement of the vial assembly will cause the fluid contained within the vial to flow past check valve 63, into passageway 30a and finally into the reservoir of the dispenser unit via inlet port 56.

It is to be noted that no vial cage is required in this form of the invention because a larger 5 ml vial is used to fill the reservoir of the dispenser unit.

Figure 58:
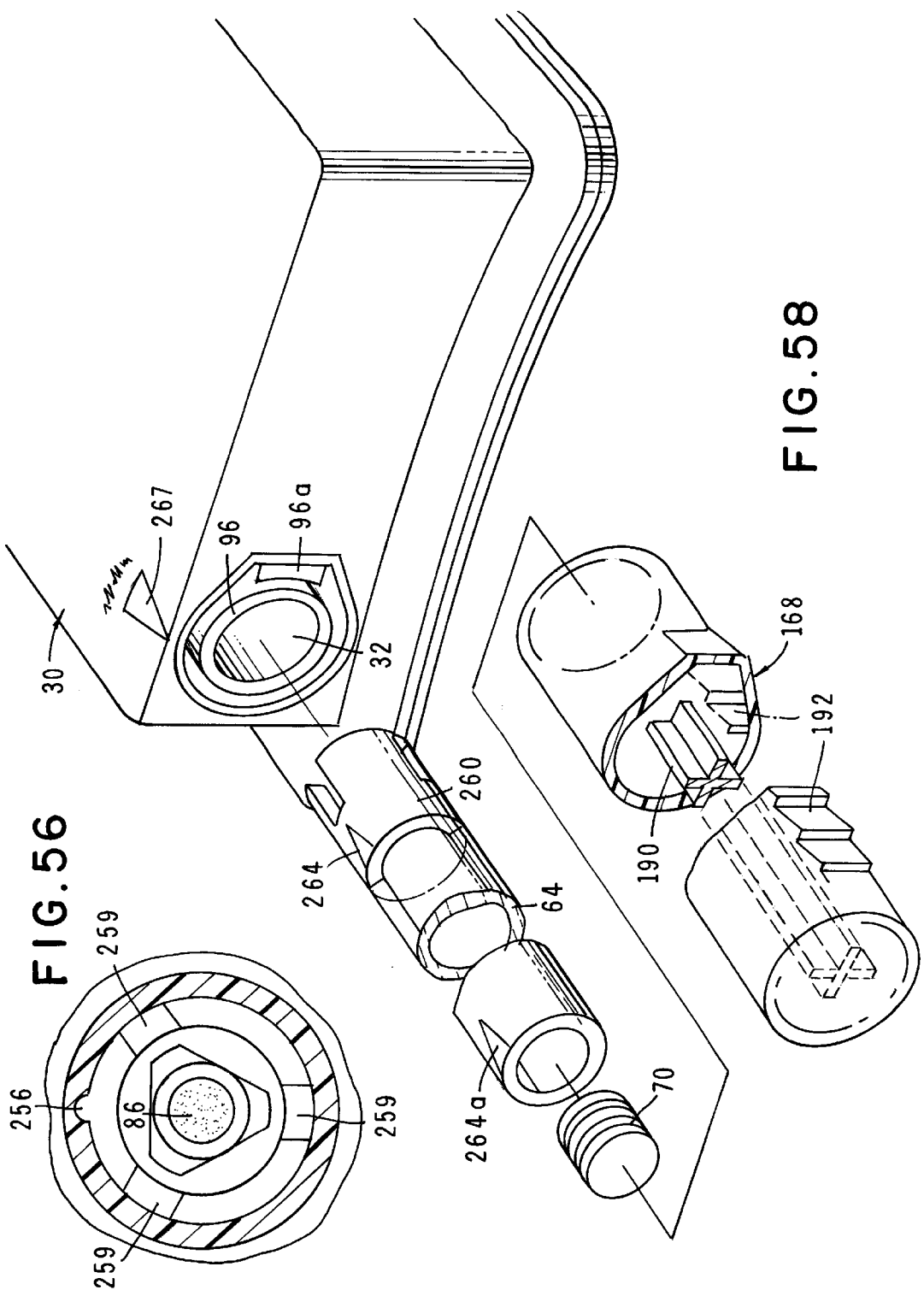
FIG. 58 is a generally perspective, exploded view of yet another embodiment of the delivery device of the present invention.
Figure 59:
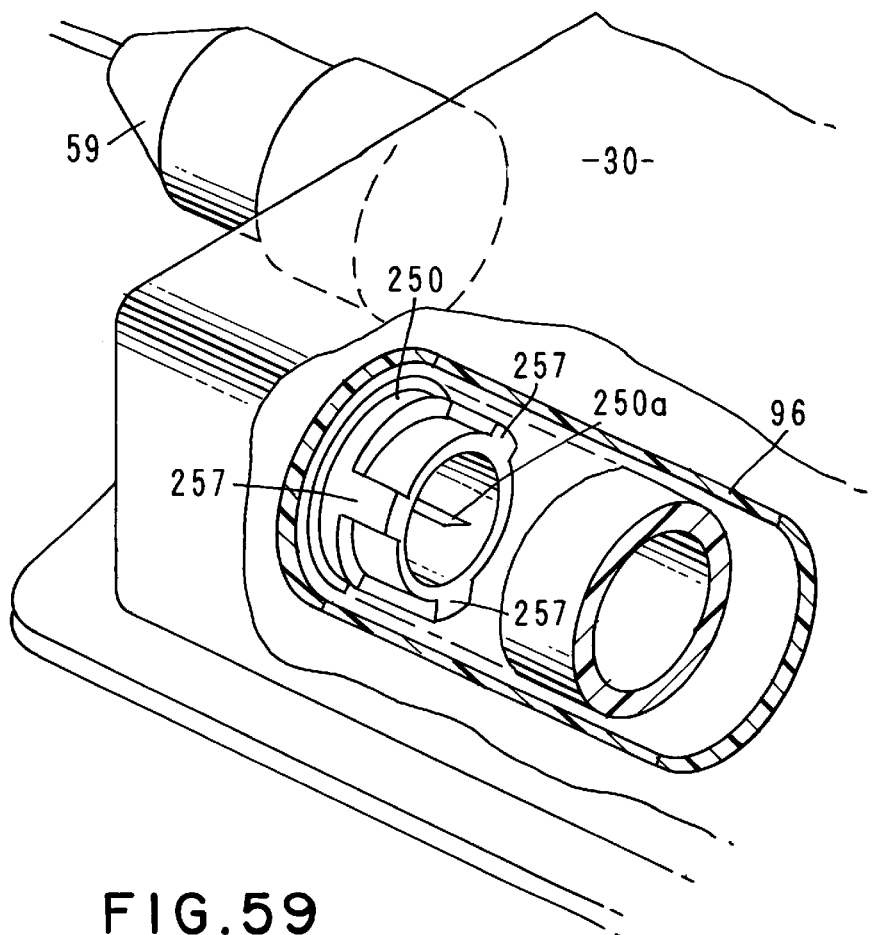
FIG. 59 is a generally perspective, fragmentary view of a position of the fluid delivery device shown in FIG. 58, illustrating the configuration of the receiving chamber of the housing of the delivery device which is adapted to receive a polarity adapter of still a slightly different construction.
Figure 60:
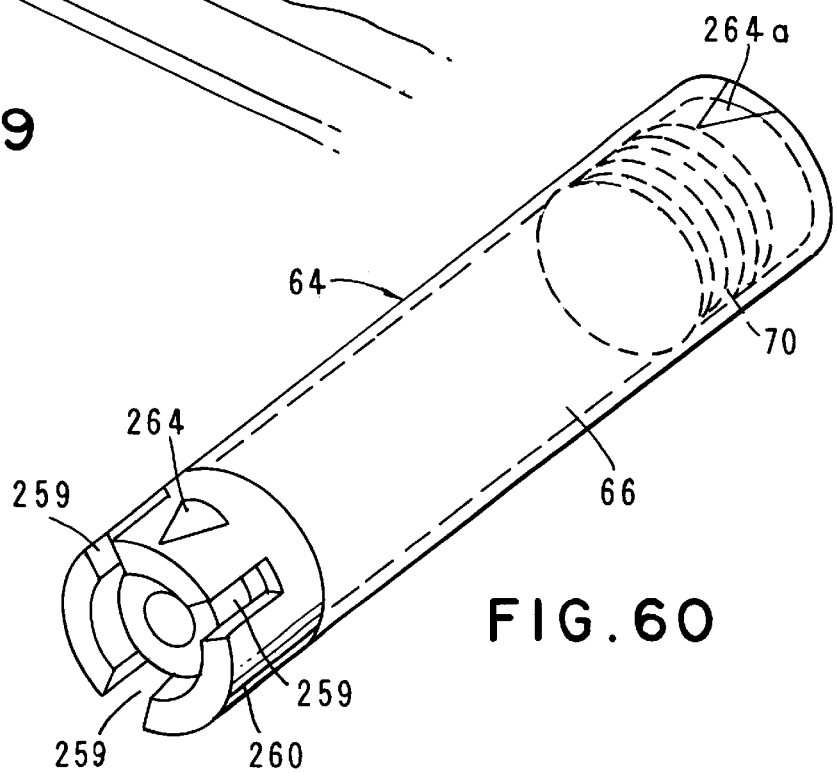
FIG. 60 is a generally perspective view of the polarity adapter and vial assembly construction that is receivable within the receiving chamber of the housing shown in FIG. 52.
Figure 61:
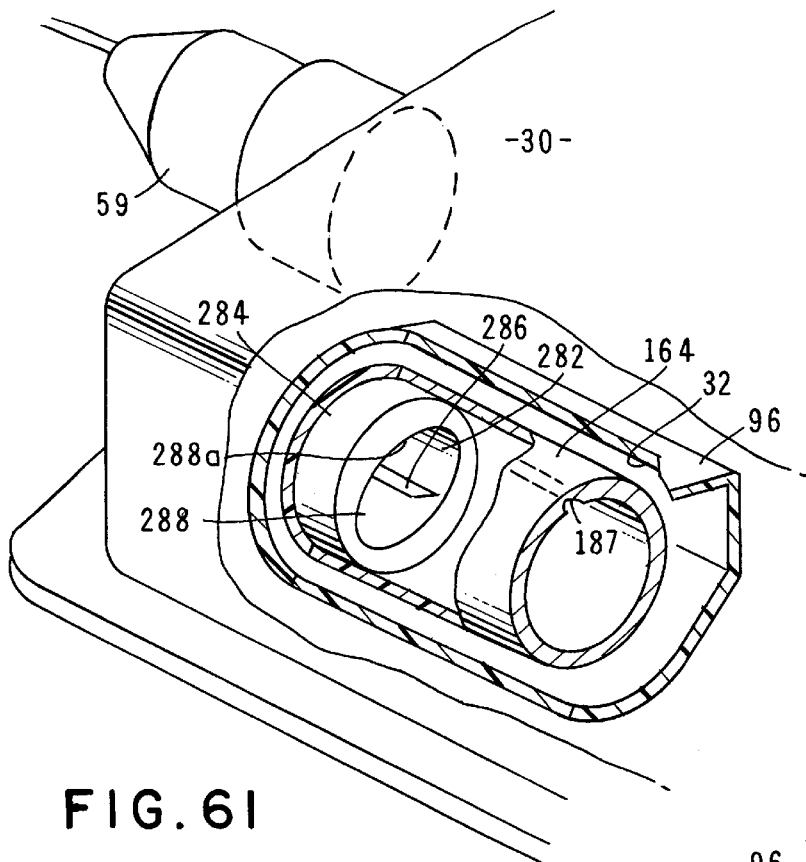
FIG. 61 is a generally perspective view of the forward portion of a delivery component of an alternate form of the fluid delivery device of the present invention.
Figure 62:
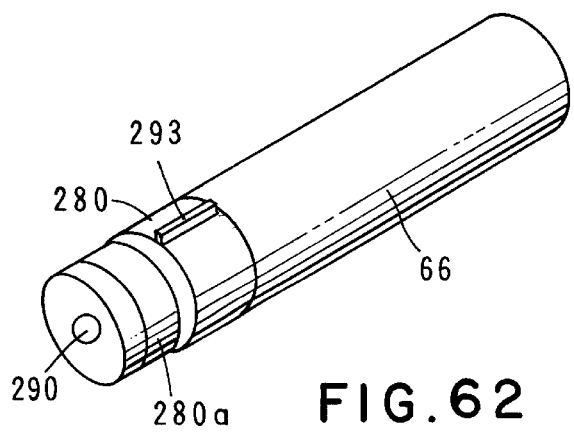
FIG. 62 is a generally perspective view of the polarity adapter and medicament containing via assembly of this latest form of the invention.
Figure 64:
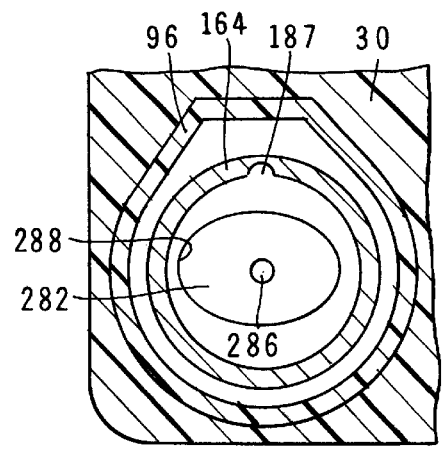
FIG. 64 is a cross-sectional view taken along lines 64—64 of FIG. 63.
Figure 67:
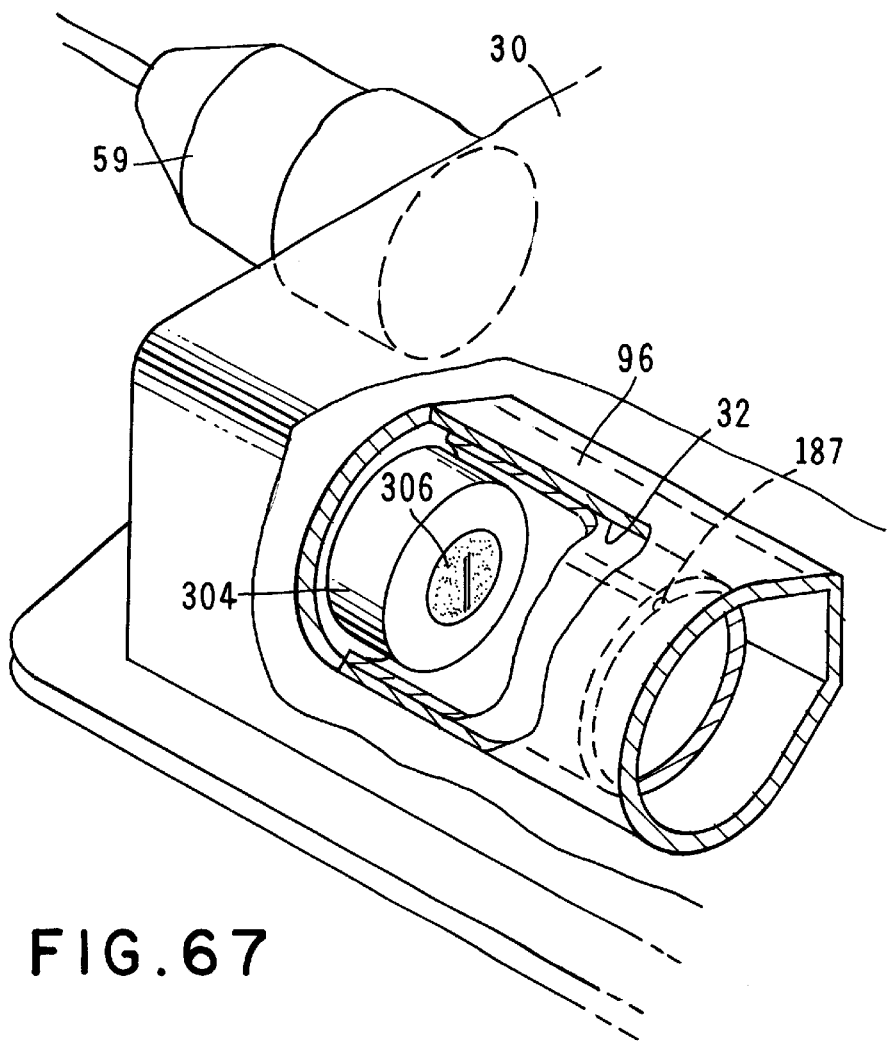
FIG. 67 is a generally perspective view of the forward portion of the delivery component of still another embodiment of the fluid delivery device of the present invention.

Referring to FIGS. 58 through 60, yet another form of the fluid delivery device of the invention is there shown. This form of the invention is very similar to that shown in FIGS. 52 through 57 and like numerals are used in FIGS. 58 through 60 to identify like components. Once again, housing assembly 30 includes an elongated receiving chamber 32 that is formed by uniquely configured liner 96 and, save for needle adapter 250, housing assembly 30 is substantially identical to that shown in FIGS. 1 through 7 and previously described herein. In this alternate form of the invention, the fill means is identical to that previously described and the polarity adapter 260 is also substantially identical to that previously described. However, in this latest form of the invention, the indexing rib 256 has been removed and has been replaced with an indexing arrow 264. A similar indexing arrow 264a is also imprinted on vial assembly 64. During the mating of the vial assembly and the polarity adapter with the dispenser housing, arrows 264 and 264a are aligned with an indexing arrow 267 imprinted on housing 30 (FIG. 58). With this arrangement, the indexing groove 234a is no longer required on sleeve 260, since the arrows will function to correctly align grooves 259 with bosses 257 to permit mating of the components.

Materials suitable for use in constructing the polarity adapter and the first and second adapter sleeves include polypropylene, acetyl copolymer, nylon, and polybutylene terephthalate available from GE Plastics of Pittsfield, Mass.

Referring now to FIGS. 61 through 66, yet another form of the fluid delivery device of the invention is there shown. This form of the invention is also similar in some respects to that shown in FIGS. 1 through 7 and like numerals are used in FIGS. 61 through 66 to identify like components. As before, the device here comprises a housing assembly 30 having an elongated receiving chamber 32. The housing assembly 30 is substantially identical to that shown in FIGS. 1 through 7 and previously described herein. This alternate form of the invention also includes a first adapter sleeve 164 that is telescopically receivable within chamber 32 and a differently configured polarity adapter 280 (FIG. 62) that is, in turn, telescopically receivable within adapter sleeve 164 in the manner indicated in the drawings.

As in the earlier described embodiments, housing assembly 30 includes a fluid reservoir for containing the medicinal fluids to be delivered to the patient. The fluid reservoir can be filled by fill means similar to that earlier described and communicates with substantially identical infusion means in the manner previously discussed herein. Housing assembly 30 also includes a fill chamber 282, which is defined by a cup-like support member 284 that supports a hollow cannula 286. As best seen by referring to FIG. 61, member 284 is uniquely configured having an elliptically shaped opening 288a. Cannula 286 extends into the interior of member 284 and is adapted to pierce the pierceable septum carried by the hub like forward portion 280a of polarity adapter 280. Portion 280a supports a hollow cannula 292 which communicates with a chamber 280b formed in hub-like portion 280a. Cannula 292 is adapted to pierce the septum 86 of the container or vial 66 which is of the character previously described having a fluid chamber 68 adapted to contain the medicament to be dispensed to the patient. As indicated in FIG. 63, when cannula 292 pierces vial septum 86, fluid communication is established between chamber 280b of hub-like portion 280a of the polarity adapter and chamber 68 of container 66.

With the components of the apparatus in the position shown in FIG. 63, an inward force exerted on the adapter sleeve 168 will cause the container subassembly and the polarity adapter to move as a unit into the position shown in FIG. 66. In this position cannula 286 pierces septum 290 of the polarity adapter, opening fluid communication between chamber 280b and the housing chamber 63a that houses umbrella check valve 63. As before a rib 293 formed on the polarity adapter (FIG. 62) is received within a groove 187 formed in adapter 164 (FIG. 61) so as to guide the assembly into seating engagement within chamber 288. In this regard it is important to note that only a polarity adapter having an elliptically shaped hub portion 280a can be received within elliptical chamber 288 and then moved into piercing engagement with cannula 286. As a result of this unique arrangement, a conventional vial assembly having a cylindrically shaped body cannot be inserted into chamber 288 and cannot be mated with cannula 286 to allow fluid flow into the fluid reservoir of the delivery component. Accordingly, only when a polarity adapter of the configuration shown in the drawings is connected to the conventional vial assembly in the manner shown in FIG. 63 and as previously described herein, can the vial assembly 64 be mated with the fluid delivery component. However, using the uniquely configured polarity adapter of this latest form of the invention, a conventional vial assembly can be conveniently mated with the fluid delivery component so that fluid contain within the vial assembly can flow through cannula 292, into chamber 280b, into cannula 286, past check valve 63 and into the delivery device fluid reservoir via passageway 30a (FIG. 66).

Turning next to FIGS. 67 through 74, still another form of the fluid delivery device of the invention is there shown. This form of the invention is similar in some respects to that shown in FIGS. 61 through 66 and like numerals are used in FIGS. 67 through 74 to identify like components. As before, the device here comprises a housing assembly 30 having an elongated receiving chamber 32. The housing assembly 30 is substantially identical to that shown in FIGS. 1 through 7 and previously described herein. This alternate form of the invention also includes a first adapter sleeve 164 that is telescopically receivable within chamber 32 and a differently configured polarity adapter 300 (FIG. 68) that is, in turn, telescopically receivable within adapter sleeve 164 in the manner indicated in the drawings.

As in the earlier described embodiments, housing assembly 30 includes a fluid reservoir for containing the medicinal fluids to be delivered to the patient. Housing assembly 30 also includes a cup-like support member 304 that supports a slit septum 306 which is pierceable by a blunt end cannula 308 that is carried by a supporting wall 300a of polarity adapter 300. To position slit septum 306 within member 304, the septum is provided with a circumferentially extending protuberence 306a that is received within a locating groove 304a formed in member 304. Wall 300a also supports a hollow cannula 310 that is adapted to pierce the septum 86 of the container or vial assembly 66 which is of the character previously described having a fluid chamber 68 that contains the medicament to be dispensed to the patient. As indicated in FIG. 69, when the polarity adapter 300 is interconnected with the assembly in the manner shown in FIG. 69, cannula 310 pierces vial septum 86 and fluid communication is established between chamber 68 of the vial assembly and the internal passageway of blunt end cannula 308.

Figure 68:
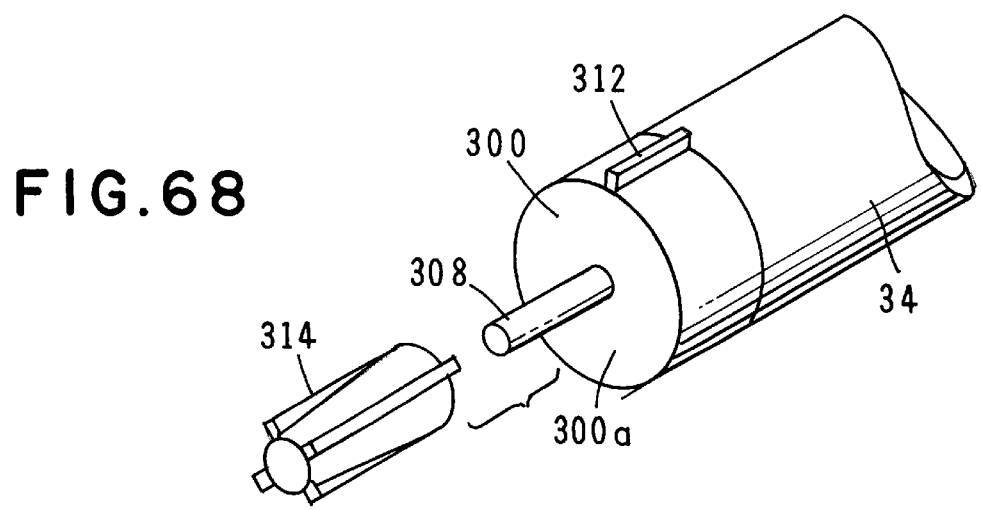
FIG. 68 is a generally perspective view of an alternate form of polarity adapter and vial assembly that is mateable with the fluid delivery device shown in FIG. 67.
Figure 69:
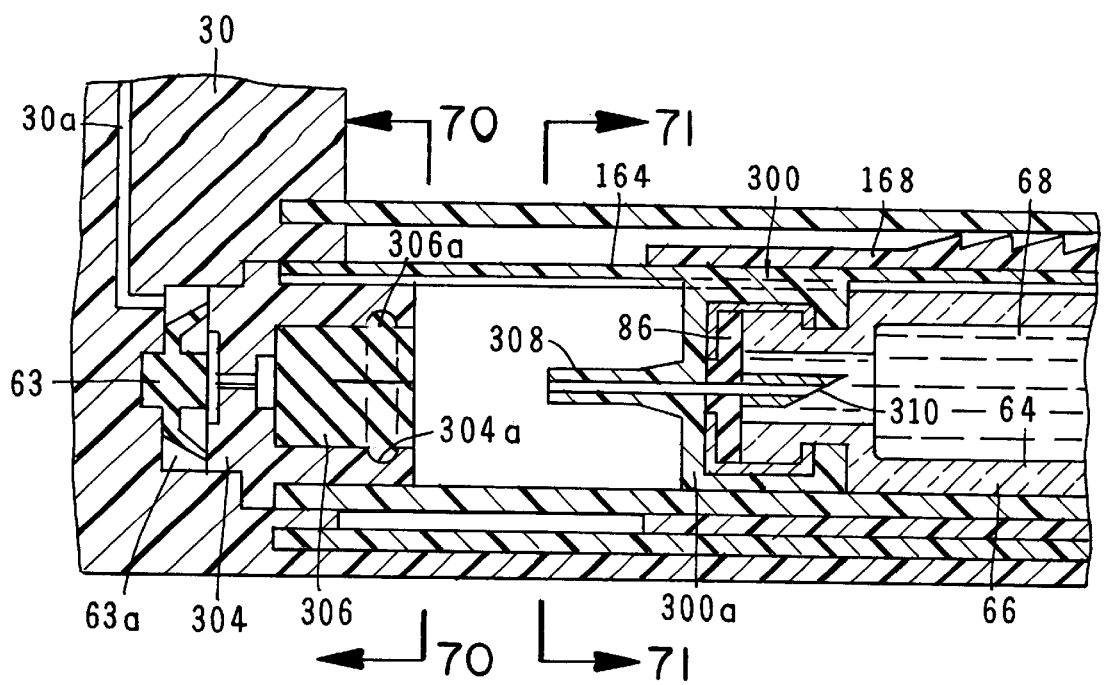
FIG. 69 is a cross-sectional view of the forward portion of the fluid delivery component showing the polarity adapter and vial assembly of this latest form of the invention mated therewith.
Figure 70:
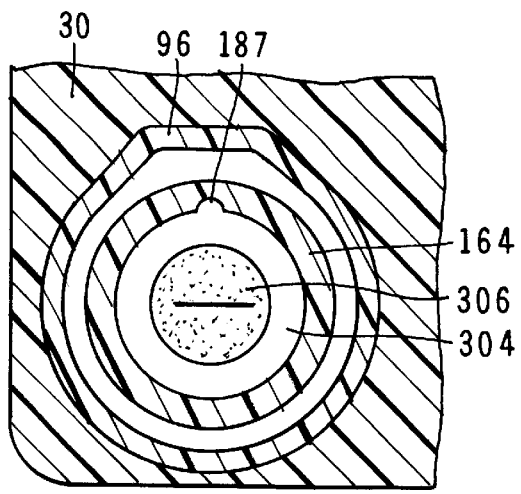
FIG. 70 is a cross-sectional view taken along lines 70—70 of FIG. 69.
Figure 71:
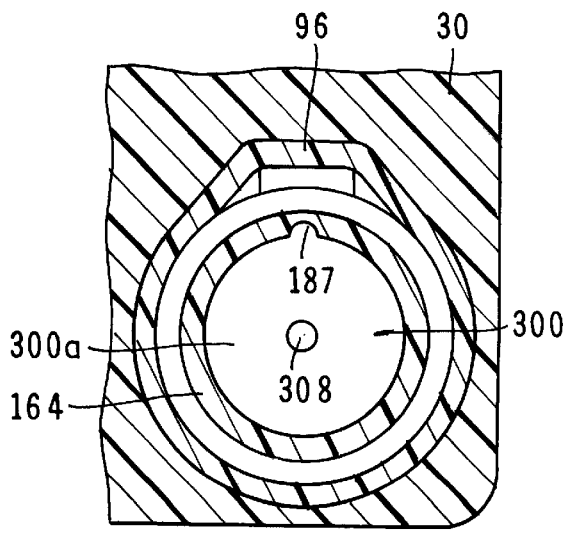
FIG. 71 is a cross-sectional view of taken along lines 71—71 of FIG. 69.
Figure 72:
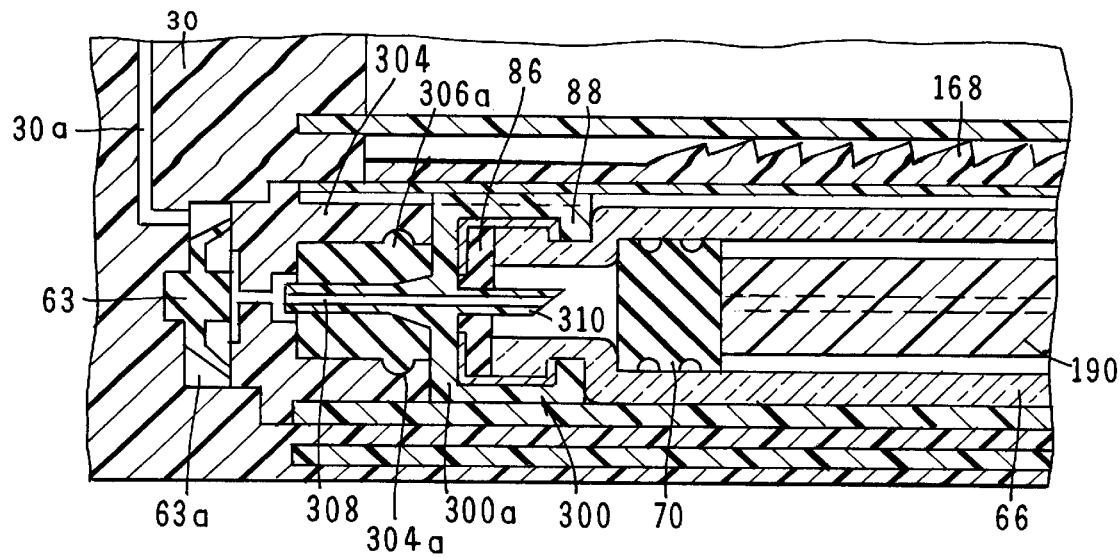
FIG. 72 is a cross-sectional view similar to FIG. 69, but showing the polarity adapter and file assembly fully inserted into the receiving chamber of the fluid delivery component.
Figure 73:
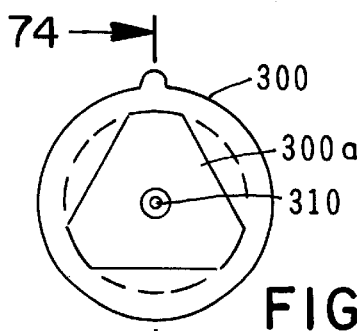
FIG. 73 is a front view of the polarity adapter of this latest embodiment of the invention.
Figure 74:
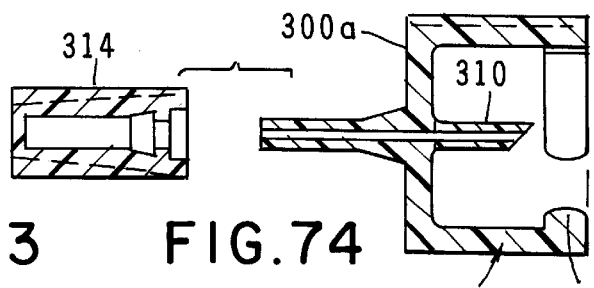
FIG. 74 is a cross-sectional view taken along lines 74—74 of FIG. 73.
Figure 75:
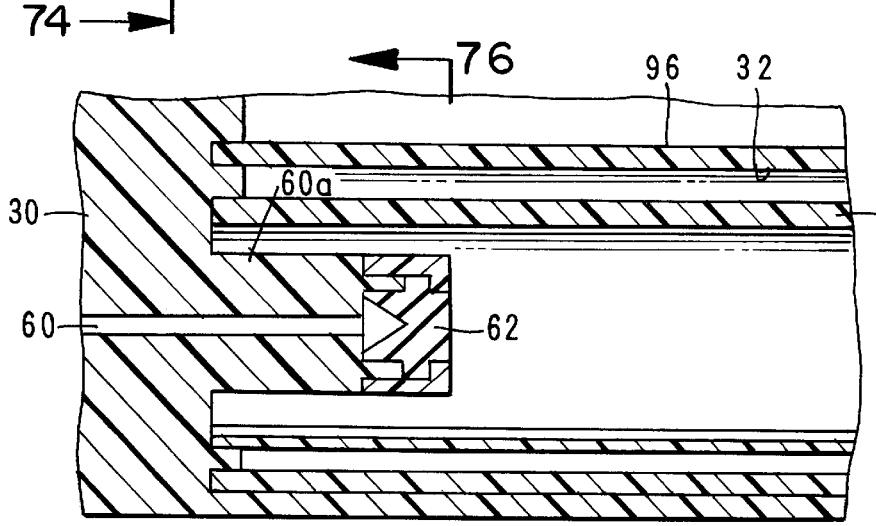
FIG. 75 is a cross-sectional view of the forward portion of the fluid delivery component of still another form of the apparatus of the present invention.
Figure 76:
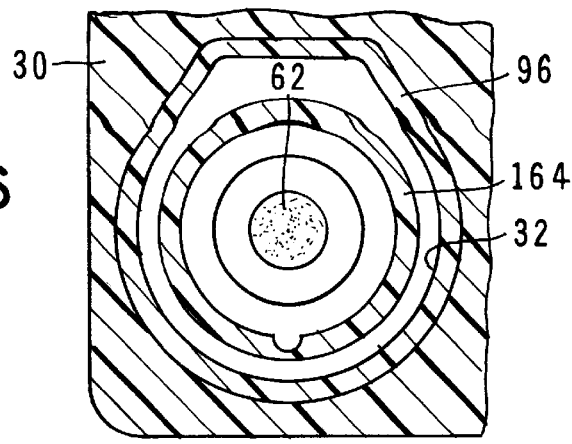
FIG. 76 is a cross-sectional view taken along lines 76—76 of FIG. 75.

With the components of the apparatus in the position shown in FIG. 69, an inward force exerted on adapter sleeve 168 will cause the container subassembly and the polarity adapter, which has been connected thereto, to move as a unit into the position shown in FIG. 72. In this position cannula 308 pierces slit septum 304 of the fluid delivery component thereby opening fluid communication between a housing chamber 63a that houses umbrella check valve 63 and passageway 30a formed in housing assembly 30. As before, a rib 312 (FIG. 68) formed on the polarity adapter is received within a groove 187 formed in adapter 164 (FIGS. 67, 70, and 71) and guides the blunt end cannula of the polarity adapter into seating engagement with slit septum 306. A sealing cap 314 is received over blunt end cannula 308 when the polarity adapter is not in use (FIG. 68).

With the construction thus described, when the polarity adapter of the configuration shown FIGS. 67 through 74 of the drawings is connected to the conventional vial assembly in the manner shown in FIG. 69 and as previously described herein, and the assemblage thus formed is mated with the fluid delivery component, fluid can be delivered to the fluid delivery component using a conventional vial assembly. More particularly, when the components are mated in a manner shown in FIG. 72, fluid contained within the vial component of the vial subassembly will flow through cannula 310, into cannula 308, past check valve 63 and into the delivery device fluid reservoir via passageway 30a of the housing of the fluid delivery component.

Turning next to FIGS. 75 through 79, yet another embodiment of the fluid delivery device of the invention is there shown. This form of the invention is also similar in some respects to that shown in FIGS. 1 through 7 and FIGS. 67 through 74 and like numerals are used in FIGS. 75 through 79 to identify like components. Once again, the device here comprises a housing assembly 30 having an elongated receiving chamber 32. The housing assembly 30 is substantially identical to that shown in FIGS. 1 through 7 and previously described herein. This alternate form of the invention also includes a first adapter sleeve 164 that is telescopically receivable within chamber 32 and a differently configured polarity adapter 320 (FIG. 78) that is, in turn, telescopically receivable within adapter sleeve 164 in the manner indicated in the drawings.

In the form of the invention shown in FIGS. 75 through 79 of the drawings, a fill chamber 60 is formed within a hub-like support member 60a and is disposed within the previously identified receiving chamber 32 of housing assembly 30. As was the case with the embodiment of the invention shown in FIGS. 1 through 7, fill chamber 60 communicates with reservoir 38 of the fluid delivery component via a conventional umbrella check valve 63 and an inlet passageway 30a (FIG. 2).

As in the earlier described embodiments, the polarity adapter 320 functions to interconnect the container or vial subassembly 34 of the apparatus with the fluid delivery device housing 30. As best seen by referring to FIGS. 77 and 78, polarity adapter 320 includes a generally tubular shaped connector housing 322 within which is mounted a novel double ended cannula component 323. As shown in FIG. 78, housing 322 has a partition wall 324 that supports a novel collapsible bellows 328 that carries the double-ended cannula, 323 which is of the character best seen in FIGS. 77 and 78. In addition to partition wall 324, the polarity adapter includes a connector portion 325 and a skirt portion 330 both of which are telescopically receivable within chamber 32 in the manner shown in FIGS. 77 and 77A.

Figure 77:
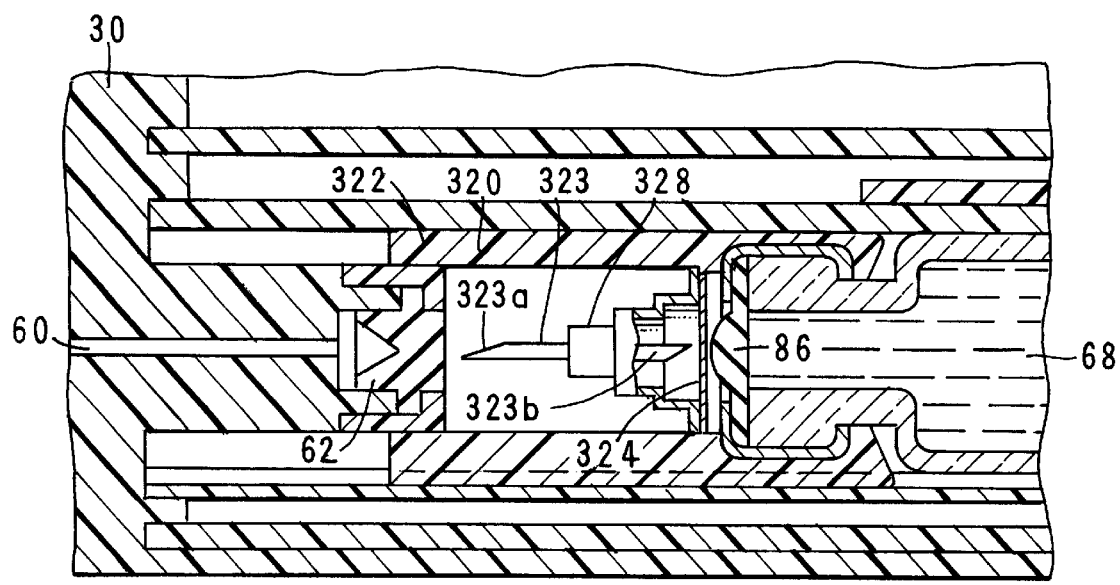
FIG. 77 is a cross-sectional view similar to FIG. 75, but showing the polarity adapter and a vial assembly of this latest form of the invention inserted into the receiving chamber of the fluid delivery device.
Figure 77B:
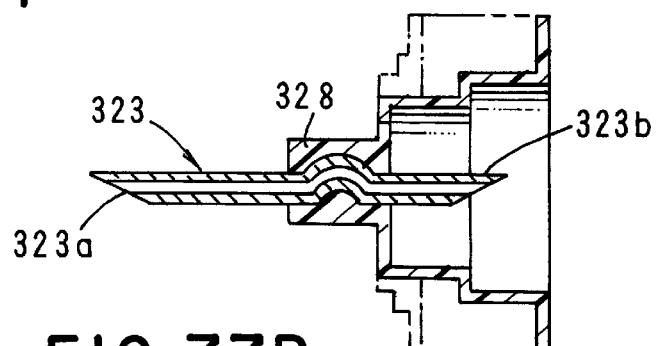
FIG. 77B is an enlarged, cross-sectional view of the polarity adapter similar to FIG. 77, showing in phantom lines the bellows in a collapsed configuration.
Figure 77A:
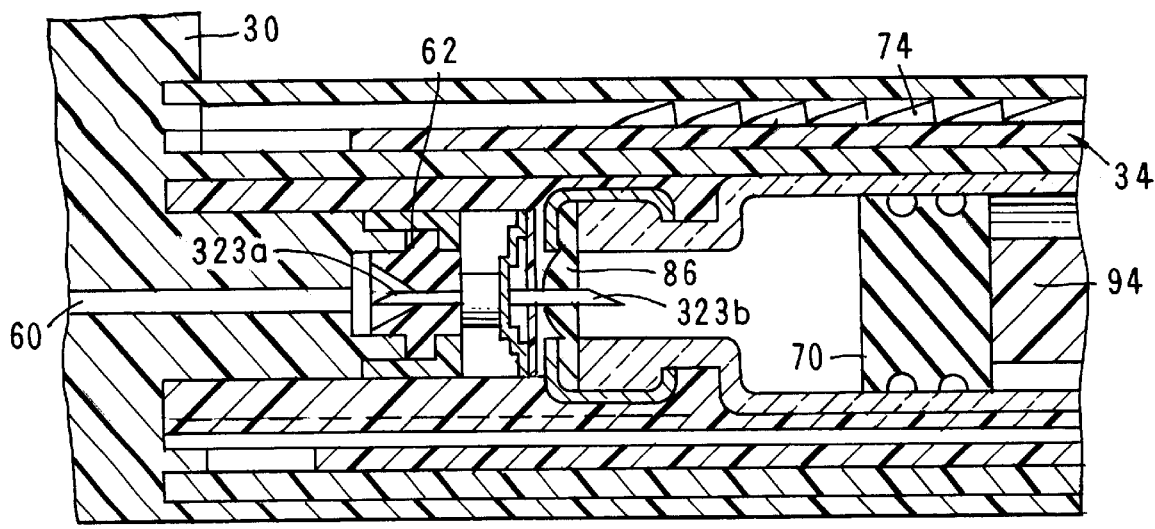
FIG. 77A a cross-sectional view similar to FIG. 77, but showing the polarity adapter and the subassembly fully inserted into the receiving chamber.
Figure 78:
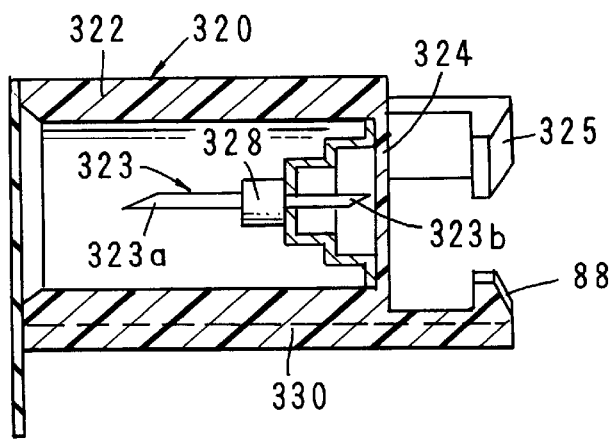
FIG. 78 is a side elevational, cross-sectional view of the polarity adapter of this latest form of the invention.
Figure 79:
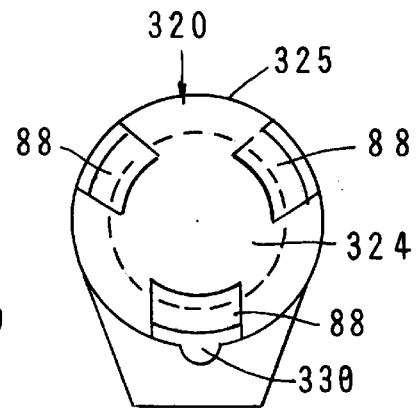
FIG. 79 is a view taken along lines 79—79 of FIG. 78.
Figure 80:
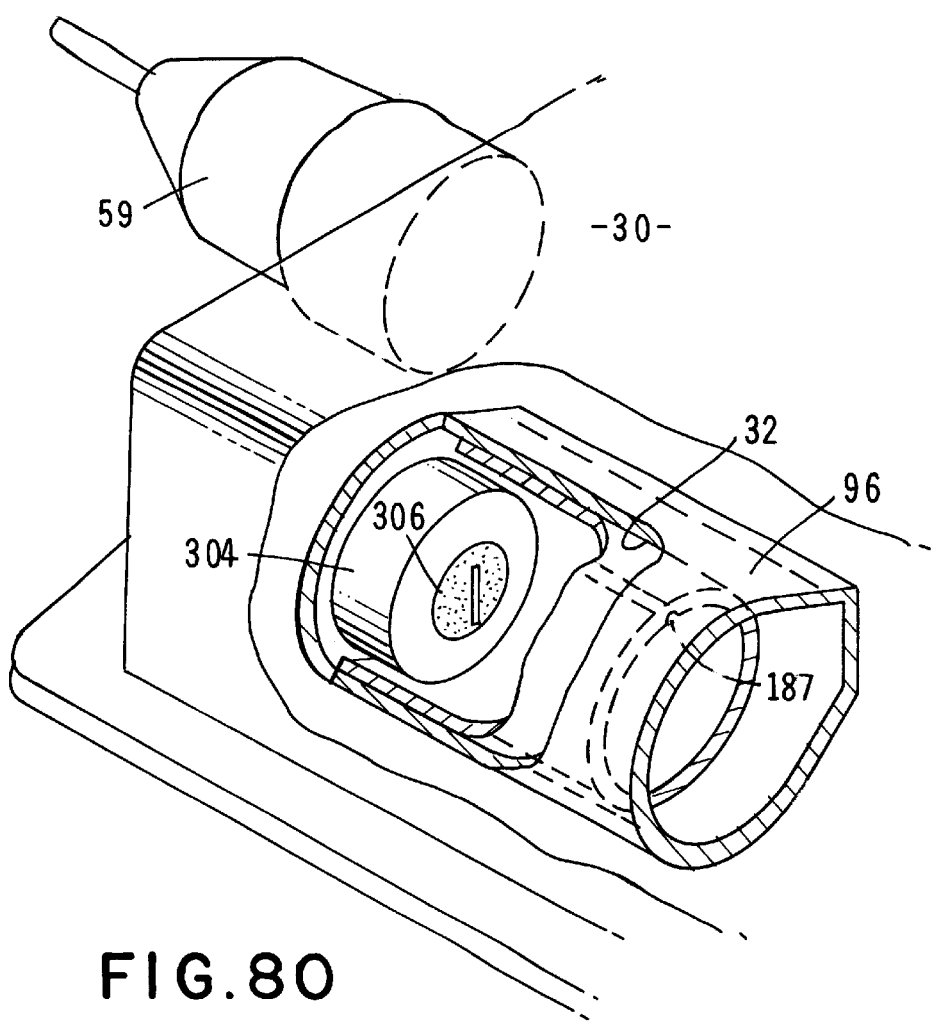
FIG. 80 is a generally perspective view of the forward portion of a fluid delivery component of yet another embodiment of the apparatus of the invention.
Figure 81:
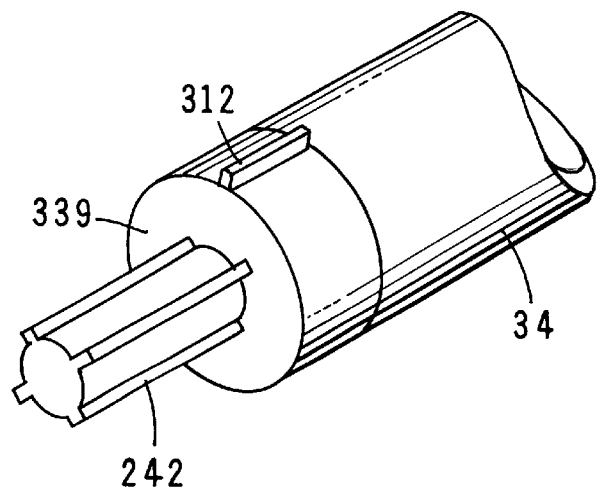
FIG. 81 is a generally perspective, fragmentary view of another form of the polarity adapter and vial assembly of this latest form of the invention.
Figure 82:
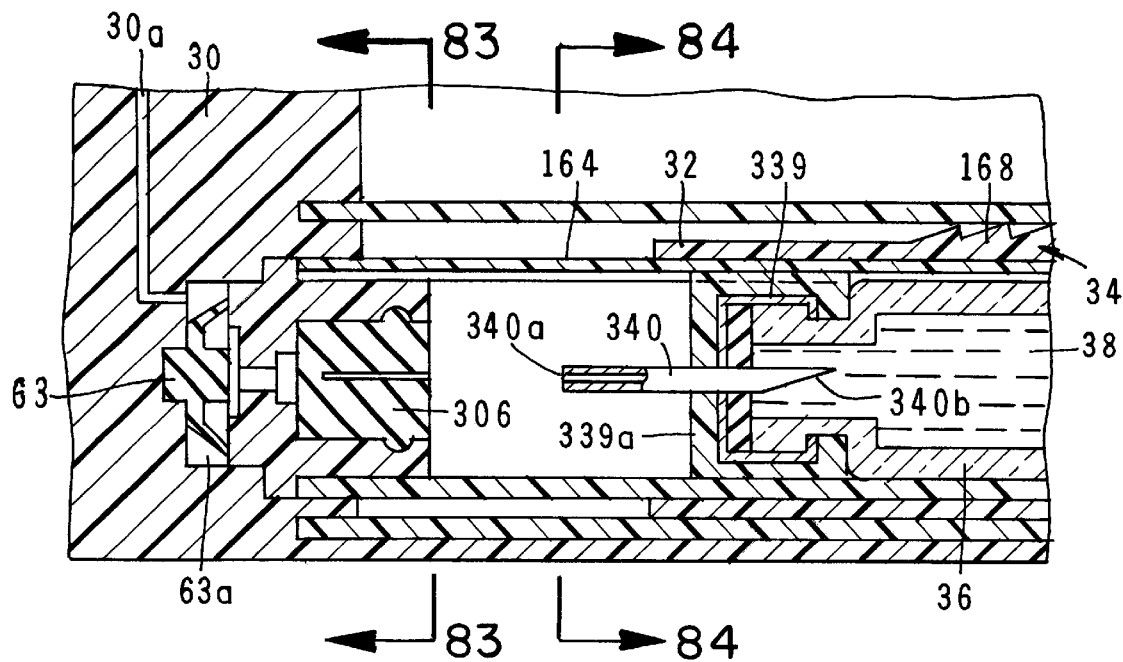
FIG. 82 is a side-elevational, cross-sectional view of the forward portion of the delivery device shown in FIG. 80, but shown at the polarity adapter and vial assembly of the apparatus inserted into the receiving chamber of the fluid delivery component.
Figure 83:
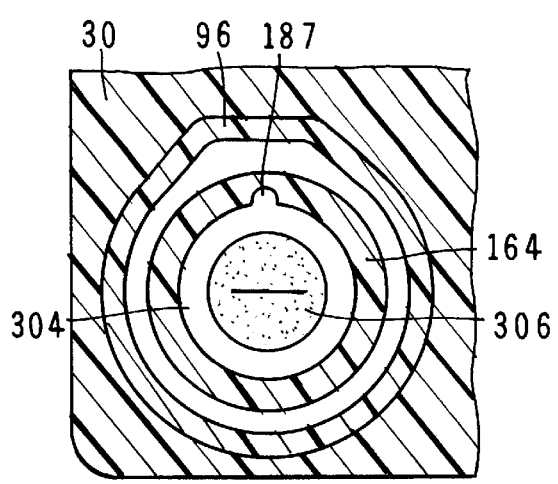
FIG. 83 is a cross-sectional view taken along lines 83—83 of FIG. 82.
Figure 84:
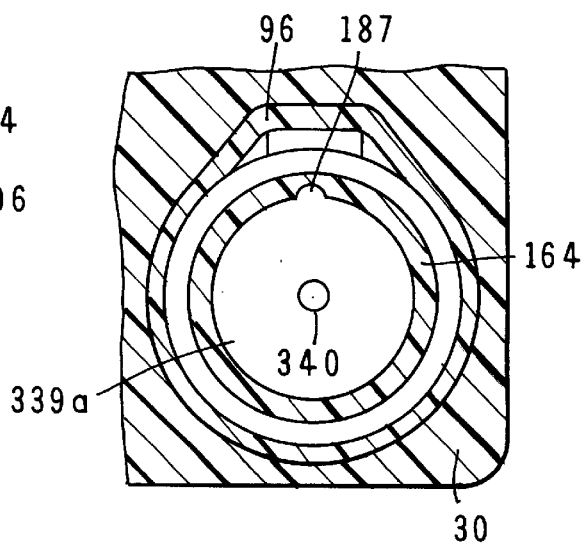
FIG. 84 is a cross-sectional view taken along lines 84—84 of FIG. 82.
Figure 85:
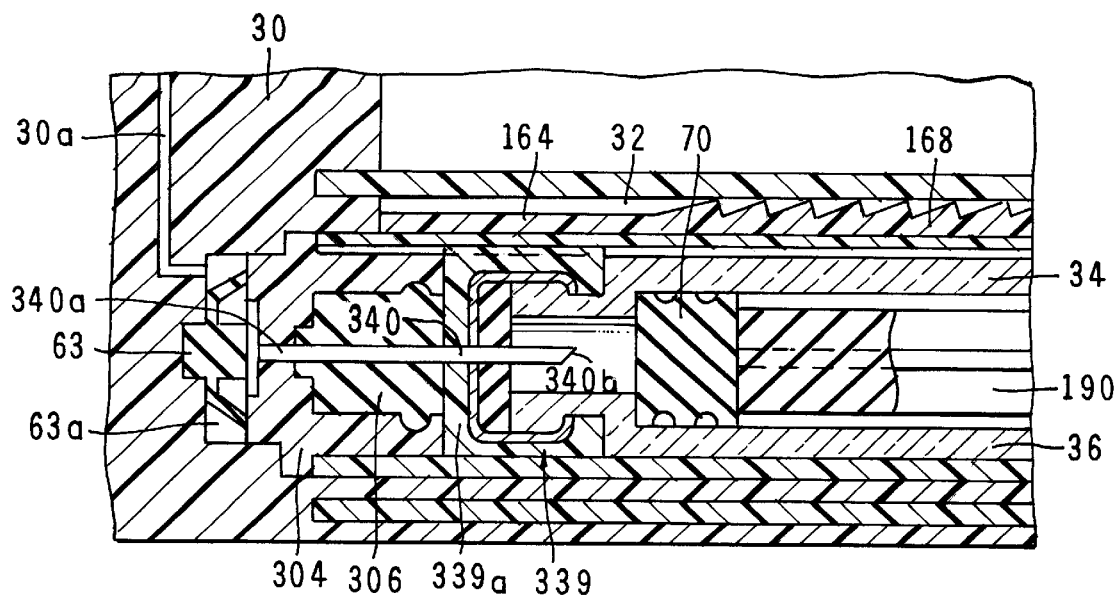
FIG. 85 is a cross-sectional view similar to FIG. 82, but showing the polarity adapter and a vial assembly fully mated with the fluid delivery component.
Figure 86:
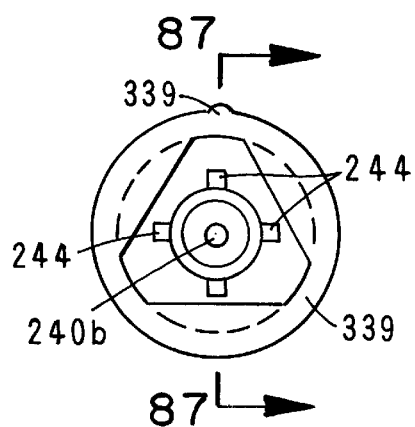
FIG. 86 is a rear view of the polarity adapter of this latest embodiment of the invention.

As shown in FIGS. 77 and 78, hollow cannula 323 has a first end 323a for piercing first septum 62 of housing assembly 30 and a second end 323b for piercing the pierceable septum 86 which forms a portion of vial subassembly 64. However, when the polarity adapter is in the configuration shown in FIG. 78, hollow cannula 323 is in a non-piercing relationship with respect to septums 62 and 86 and container assembly 34 can be interconnected with the polarity adapter in the manner shown in FIG. 77 with the hollow cannula remaining in its nonpiercing configuration. Once again protuberances 88 formed on the polarity adapter will securely grip the neck portion of the container subassembly in the manner shown in FIG. 77. It is to be understood that protuberances 88 can be of various configurations and geometries for use in securing the polarity adapter to the vial. In this configuration the assembly to made up of the polarity adapter and the container subassembly can be inserted into the receiving chamber of the fluid delivery component in a manner shown in FIG. 77. When the container assembly is urged inwardly to the position shown in FIG. 77A bellows 328 will deform and collapse causing end 323b of cannula 323 to pierce septum 86 of the container subassembly and causing end 323a of the cannula to pierce septum 62 of the fluid delivery component.

With the component parts of the apparatus in the position shown in FIG. 77A, fluid communication is established between fluid chamber 68 of the container 66 and the chamber 60 of the fluid delivery component via double ended cannula 323. An inward movement of the adapter sleeve 74 will then cause pusher member 94 (FIG. 77a) of adapter sleeve 74 to urge plunger 70 inwardly of vial 66 causing the fluid contained within the vial to flow through hollow cannula 323, into fill chamber 60 and then into the fluid reservoir of the fluid delivery component via passageway 30a.(see FIGS. 1 and 77A)

Figure 87:
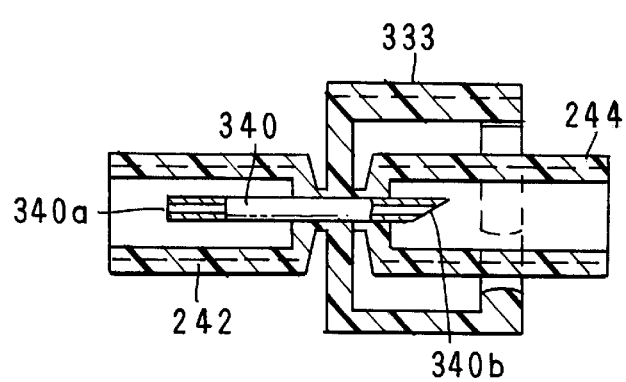
FIG. 87 is a cross-sectional view taken along lines 87—87 of FIG. 86.

Referring next to FIGS. 80 through 87, yet another embodiment of the invention is there illustrated. This latest embodiment of the invention is virtually identical in construction and operation to that shown in FIGS. 67 through 74. Accordingly, like numbers are used in FIGS. 80 through 87 to identify like components shown in FIGS. 67 through 74. The primary difference between this latest embodiment of the invention and that shown in FIGS. 67 through 74 resides in the configuration of the hollow cannula carried by the polarity adapter 339 (FIG. 87). This hollow cannula, which is identified by the numeral 340 is carried by a wall 339a and preferably is of a one-piece construction made of steel. The first end 340a of the cannula is blunt ended and is adapted to pierce slit septum 306 of the fluid delivery component. The opposite end 340b of the cannula is sharpened and is adapted to pierce pierceable septum 86 of the vial subassembly 64. Twist off caps 242 and 244 protect the cannula from contamination.(FIG. 87)

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A fluid delivery device for infusing medicinal fluids into a patient at a controlled rate comprising:
   (a) a housing including a receiving chamber and a pierceable septum disposed within said receiving chamber;
   (b) a fluid reservoir disposed within said housing for containing the medicinal fluids to be delivered to the patient, said delivery device reservoir having an inlet in communication with said fill chamber and an outlet;
   (c) stored energy means cooperatively associated with said fluid reservoir for urging fluid flow through said outlet of said reservoir;
   (d) fill means connected to said housing for filling said fluid reservoir, said fill means including a container subassembly comprising a container including a body portion having a fluid chamber and a pierceable septum connected to said body portion for sealably closing said fluid chamber; and (e) a polarity adapter assembly for interconnecting said container subassembly with said housing, said polarity adapter assembly including a hollow cannula having a first end for piercing said first pierceable septum of said container assembly and a second end for piercing said septum of said housing.

2. The fluid delivery device as defined in claim 1 in which said housing of said fluid delivery device is provided with a plurality of grooves and in which said polarity adapter assembly further comprises a connector housing having a plurality of tongues receivable within said grooves.

3. The fluid delivery device as defined in claim 1, further including a connector housing having a partition wall, said hollow cannula being supported by said partition wall.

4. A polarity adapter for interconnecting a container having a first pierceable septum with a fluid delivery device having a receiving chamber and a second pierceable septum disposed within said receiving chamber, said polarity adapter comprising:

(a) a connector housing having an outer wall and an internal partition wall connected to said outer wall; and (b) a hollow cannula supported by said partition wall, said hollow cannula having a first end for piercing said first pierceable septum and a second end for piercing said second pierceable septum.

5. A polarity adapter as defined in claim 4 in which said fluid delivery device further includes a first adapter sleeve having a plurality of grooves and in which said connector housing of said polarity adapter is provided with a plurality of tongues receivable within said grooves.

6. A polarity adapter as defined in claim 5 in which said connector housing of said polarity adapter has the cross-sectional shape of a truncated teardrop.

7. A polarity adapter as defined in claim 6 in which said first adapter sleeve of said fluid delivery device has the cross-sectional shape of a truncated teardrop.

8. A polarity adapter as defined in claim 6 in which said partition wall of said connector housing is provided with a central aperture, at least a portion of said hollow cannula being receivable within said central aperture of said partition wall.

9. A polarity adapter as defined in claim 8 further including a needle retaining plate received within said connector housing for retaining said hollow cannula therewithin.

10. A fluid delivery device for infusing medicinal fluids into a patient at a controlled rate comprising:

(a) a housing including a fill chamber sealably closed by a first pierceable septum;

(b) a fluid reservoir disposed within said housing for containing the medicinal fluids to be delivered to the patient, said delivery device reservoir having an inlet in communication with said fill chamber and an outlet;

(c) stored energy means cooperatively associated with said delivery device reservoir and being movable between first and second positions for urging fluid flow through said outlet of said reservoir;

(d) infusion means for infusing medicinal fluids from said delivery device fluid reservoir into the patient, said infusion means being in communication with said outlet of said delivery device reservoir;

(e) fill means connected to said housing for filling said delivery device reservoir, said fill means including a container subassembly comprising a container including a body portion having a fluid chamber and a plunger telescopically movable within said fluid chamber from a first location to a second, spaced-apart location, said container subassembly further including a second pierceable septum connected to said body portion; and (f) a polarity adapter assembly for interconnecting said container assembly with said housing, said polarity adapter assembly including a hollow cannula having a first end for piercing said first pierceable septum and a second end for piercing said second pierceable septum.

11. The device as defined in claim 10 in which said housing includes a receiving chamber and a first adapter sleeve receivable within said receiving chamber, said first adapter sleeve having a first open end for telescopically receiving said polarity adapter assembly and part of said body portion of said container of said container subassembly.

12. The device as defined in claim 11 further including a second adapter sleeve telescopically receivable within said receiving chamber, said second adapter sleeve including pusher means for engagement with said plunger of said container assembly to move said plunger within said container between said first and second locations.

13. The device as defined in claim 12 in which said first adapter sleeve is provided with a plurality of grooves and in which said polarity adapter comprises a plurality of tongues receivable within said grooves.

14. The device as defined in claim 12 in which said polarity adapter assembly comprises a connector housing having an internal supporting wall for supporting said hollow cannula.

15. A device as defined in claim 14 in which said connector housing of said polarity adapter assembly is generally tear-shaped in cross section and in which said first adapter sleeve is generally tear-shaped in cross section.

16. A device as defined in claim 15 in which said receiving chamber of said fluid delivery device includes an inwardly extending locking tab and in which said second adapter sleeve further includes a plurality of locking teeth engagable by said locking tab.

17. A device as defined in claim 14 in which said connector housing comprises first and second portions interconnected by a living hinge.

18. A fluid delivery device for infusing medicinal fluids into a patient at a controlled rate comprising:

(a) a housing having an elongated receiving chamber and including (i) a fill chamber disposed within said receiving chamber said fill chamber being sealably closed by a first pierceable septum;

(ii) a first adapter sleeve receivable within said receiving chamber;

(b) a fluid reservoir disposed within said housing for containing the medicinal fluids to be delivered to the patient, said delivery device reservoir having an inlet in communication with said fill chamber and an outlet;

(c) stored energy means cooperatively associated with said delivery device reservoir and being movable between first and second positions for urging fluid flow through said outlet of said reservoir;

(d) infusion means for infusing medicinal fluids from said delivery device fluid reservoir into the patient, said infusion means being in communication with said outlet of said delivery device reservoir;

(e) fill means connected to said housing for filling said delivery device reservoir, said fill means including a container subassembly comprising a vial including a body portion having a fluid chamber and a plunger telescopically movable within said fluid chamber from a first location to a second, spaced-apart location, said container assembly further including a second pierceable septum connected to said body portion; and (f) a polarity adapter assembly connected to said container subassembly for interconnecting said container subassembly with said housing, said polarity adapter assembly including:
  (i) a connector housing; and
  (ii) a double-ended cannula component connected to said connector housing, said hollow cannula having a first end for piercing said first pierceable septum and a second end for piercing said second pierceable septum.

19. The device as defined in claim 22 further including a second adapter sleeve telescopically receivable within said receiving chamber, said second adapter sleeve including pusher means for engagement with said plunger of said container subassembly to move said plunger within said container between said first and second locations.

20. The device as defined in claim 18 in which said first adapter sleeve is provided with at least one groove and in which said polarity adapter assembly comprises at least one tongue receivable within said groove.

21. The device as defined in claim 18 in which said polarity adapter assembly is connected to said container assembly by a plastic heat shrink sleeve.

22. The device as defined in claim 18 in which said connector housing of said polarity adapter assembly is generally tear-shaped in cross section and in which said first adapter sleeve is generally tear-shaped in cross section.

23. The device as defined in claim 18 in which said connector housing of said polarity adapter assembly comprises first and second portions interconnected by a living hinge.

24. The device as defined in claim 18 further including fluid flow control means for controlling fluid flow from said reservoir toward said infusion means.

25. The device as defined in claim 24 in which said fluid flow control means comprises a filter element for filtering gases and particulate matter from fluid flowing from said reservoir. said container assembly and a second end for piercing said septum of said housing.

26. A fluid delivery device for infusing medicinal fluids into a patient at a controlled rate comprising:
  (a) a housing including a receiving chamber;
  (b) a fluid reservoir disposed within said housing for containing the medicinal fluids to be delivered to the patient, said delivery device reservoir having an inlet in communication with said receiving chamber and an outlet;
  (c) stored energy means cooperatively associated with said fluid reservoir for urging fluid flow through said outlet of said reservoir;
  (d) fill means connected to said housing for filling said fluid reservoir, said fill means including a container subassembly comprising a container including a body portion having a fluid chamber and a pierceable septum connected to said body portion for sealably closing said fluid chamber;
  (e) a polarity adapter assembly for interconnecting said container subassembly with said housing, said polarity adapter assembly including a hollow cannula having a first end for piercing said first pierceable septum of said container assembly;
  (f) a connector housing having a partition wall, said hollow cannula being supported by said partition wall; and
  (g) an adapter sleeve telescopically receivable within said receiving chamber, said adapter sleeve being configured to telescopically accept said connector housing of said polarity adapter.

27. The fluid device as defined in claim 26 in which said connector housing of said polarity adapter has the cross-sectional shape of a truncated teardrop.

28. The fluid delivery devise as defined in claim 27 in which said adapter sleeve of said fluid delivery device has the cross-sectional shape of a truncated teardrop.

29. The fluid delivery device as defined in claim 28 in which said receiving chamber of said housing has the cross-sectional shape of a truncated teardrop.

30. A fluid delivery device for infusing medicinal fluids into a patient at a controlled rate comprising:
  (a) a housing including a receiving chamber and a pierceable septum disposed within said receiving chamber;
  (b) a support member disposed within said receiving chamber;
  (c) a fluid reservoir disposed within said housing in communication with said support member;
  (d) stored energy means cooperatively associated with said fluid reservoir for urging fluid flow therefrom;
  (e) fill means connected to said housing for filling said fluid reservoir, said fill means including a container subassembly comprising a container having a body portion provided with a fluid chamber and a pierceable septum connected to said body portion for sealably closing said fluid chamber; and
  (f) a polarity adapter assembly for interconnecting said container assembly with said housing, said polarity adapter assembly including a hollow cannula having an end for piercing said first pierceable septum of said container assembly and an end for piercing said pierceable septum of said housing.

* * * * *